United States Patent [19]
Kinet et al.

[11] Patent Number: 6,165,744
[45] Date of Patent: Dec. 26, 2000

[54] ISOLATION AND CHARACTERIZATION OF CDNAS CODING FOR THE α, β, AND γ SUBUNITS OF THE HIGH-AFFINITY RECEPTOR FOR IMMUNOGLOBULIN E

[75] Inventors: Jean-Pierre Kinet, Bethesda; Henry Metzger, Chevy Chase, both of Md.

[73] Assignee: The United States of America as represented by the Department of Health and Human Services, Washington, D.C.

[21] Appl. No.: 07/626,704

[22] Filed: Dec. 14, 1990

Related U.S. Application Data

[63] Continuation-in-part of application No. 07/259,065, Oct. 18, 1988, abandoned, which is a continuation-in-part of application No. 07/160,457, Feb. 24, 1988, Pat. No. 5,639,660, and a continuation-in-part of application No. 07/240,692, Sep. 6, 1988, abandoned.

[51] Int. Cl.[7] .......................... C07K 14/705; C12N 15/12
[52] U.S. Cl. .................. 435/69.1; 435/252.3; 435/320.1; 530/350; 536/23.5
[58] Field of Search ................................ 435/69.1, 252.3, 435/320.1; 536/27, 23.5; 530/350

[56] References Cited

PUBLICATIONS

Am. Rev. Immunol. 4:419–430, 1986, Metzger et al. The Receptor with High Affinity for Immunoglobulin E.
Nature 313:806–809, Feb. 28, 1985, Jacoby et al. Isolation and Characterization of Genome and cDNA Clones of Human Erythropoietic.
Biochem. 24: 4117–24, 1985, Kinet et al. Dissociation of the Receptor for Immunoglobulin E in Mild Detergents.
Biochemistry 24:7342–48, 1985, Kinet et al. Noncovalently and Covalently Bound Lipid on the Receptor for Immunoglobulin E.
J. Biol. Chem. 259:14922–27, Alcaraz et al. Phase Separation of the Receptor for Immunoglobulin E and Its Subunits in Triton X–114.

*Primary Examiner*—John Ulm
*Attorney, Agent, or Firm*—Klarquist Sparkman Campbell Leigh & Whinston,LLP

[57] ABSTRACT

The present invention relates to DNA segments encoding the α, β, and γ subunits of the high affinity receptor for immunoglobulin E (IgE). The invention further relates to a method of producing the receptor by expressing cDNA for its α, β, and γ subunits in a host cell simultaneously.

28 Claims, 26 Drawing Sheets

FIG. 1A

```
TACTAAGAGT CTCCAGCATC CTCCACCTGT CTACCACCGA GCATGGGCCT ATATTTGAAG      60

CCTTAGATCT CTCCAGCACA GTAAGCACCA GGAGTCCATG AAGAAG ATG GCT CCT        115
                                             Met Ala Pro
                                               1

GCC ATG GAA TCC CCT ACT CTA CTG TGT GTA GCC TTA CTG TTC TTC GCT        163
Ala Met Glu Ser Pro Thr Leu Leu Cys Val Ala Leu Leu Phe Phe Ala
 5                  10                      15

CCA GAT GGC GTG TTA GCA GTC CCT CAG AAA CCT AAG GTC TCC TTG AAC        211
Pro Asp Gly Val Leu Ala Val Pro Gln Lys Pro Lys Val Ser Leu Asn
 20                  25                      30                  35

CCT CCA AAT AGA ATA TTT AAA GGA GAG AAT GTG ACT CTT ACA TGT            259
Pro Pro Asn Arg Ile Phe Lys Gly Glu Asn Val Thr Leu Thr Cys
         40                  45                      50

AAT GGG AAC AAT TTC TTT GAA GTC AGT TCC ACC AAA TGG TTC CAC AAT        307
Asn Gly Asn Asn Phe Phe Glu Val Ser Ser Thr Lys Trp Phe His Asn
             55                  60                      65

GGC AGC CTT TCA GAA GAG ACA AAT TCA AGT TTG AAT ATT GTG AAT GCC        355
Gly Ser Leu Ser Glu Glu Thr Asn Ser Ser Leu Asn Ile Val Asn Ala
 70                  75                      80
```

FIG. 1B

```
AAA TTT GAA GAC AGT GGA GAA TAC AAA TGT CAG CAC CAA CAA GTT AAT
Lys Phe Glu Asp Ser Gly Glu Tyr Lys Cys Gln His Gln Gln Val Asn    403
 85                  90                  95

GAG AGT GAA CCT GTG TAC CTG GAA GTC TTC AGT GAC TGG CTG CTC CTT
Glu Ser Glu Pro Val Tyr Leu Glu Val Phe Ser Asp Trp Leu Leu Leu    451
100                 105                 110                 115

CAG GCC TCT GCT GAG GTG ATG GAG GGC CAG CCC CTC TTC CTC AGG
Gln Ala Ser Ala Glu Val Met Glu Gly Gln Pro Leu Phe Leu Arg        499
        120                 125                 130

TGC CAT GGT AGG AAC TGG GAT GTG TAC AAG GTG ATC TAT TAT AAG
Cys His Gly Arg Asn Trp Asp Val Tyr Lys Val Ile Tyr Tyr Lys        547
        135                 140                 145

GAT GGT GAA GCT CTC AAG TAC TGG TAT GAG AAC CAC ATC TCC ATT
Asp Gly Glu Ala Leu Lys Tyr Trp Tyr Glu Asn His Ile Ser Ile        595
        150                 155                 160

ACA AAT GCC ACA GTT GAA GAC AGT GGA ACC TAC TAC TGT ACG GGC AAA
Thr Asn Ala Thr Val Glu Asp Ser Gly Thr Tyr Tyr Cys Thr Gly Lys    643
165                 170                 175

GTG TGG CAG CTG GAC TAT GAG TCT GAG CCC CTC AAC ATT ACT GTA ATA
Val Trp Gln Leu Asp Tyr Glu Ser Glu Pro Leu Asn Ile Thr Val Ile    691
180                 185                 190                 195
```

FIG. 1C

```
AAA GCT CCG CGT GAG AAG TAC TGG CTA CAA TTT TTT ATC CCA TTG TTG      739
Lys Ala Pro Arg Glu Lys Tyr Trp Leu Gln Phe Phe Ile Pro Leu Leu
                200                         205                 210

GTG GTG ATT CTG TTT GCT GTG GAC ACA GGA TTA TTT ATC TCA ACT CAG      787
Val Val Ile Leu Phe Ala Val Asp Thr Gly Leu Phe Ile Ser Thr Gln
                215                         220                 225

CAG CAG GTC ACA TTT CTC TTG AAG ATT AAG AGA ACC AGG AAA GGC TTC      835
Gln Gln Val Thr Phe Leu Leu Lys Ile Lys Arg Thr Arg Lys Gly Phe
                230                         235                 240

AGA CTT CTG AAC CCA CAT CCT AAG CCA AAC CCC AAA AAC AAC TGATATAATT   887
Arg Leu Leu Asn Pro His Pro Lys Pro Asn Pro Lys Asn Asn
                245                         250                 255

ACTCAAGAAA TATTTGCAAC ATTAGTTTTT TTCCAGCCATC AGCAATTGCT ACTCAATTGT    947

CAAACACAGC TTGCAATATA CATAGAAACG TCTGTGCTCA AGGATTTATA GAAATGCTTC    1007

ATTAAACTGA GTGAAACTGG TTAAGTGGCA TGTAATAGTA AGTGCTCAAT TAACATTGGT    1067

TGAATAAATG AGAGAATGAA TAGATTCATT TATTAGCATT GTAAAAGAGA TGTTCAATTT    1127

CAATAAAATA AATATAAAAC CATGTAAAAA AAAAAAAAAA AAAAAAA                  1174
```

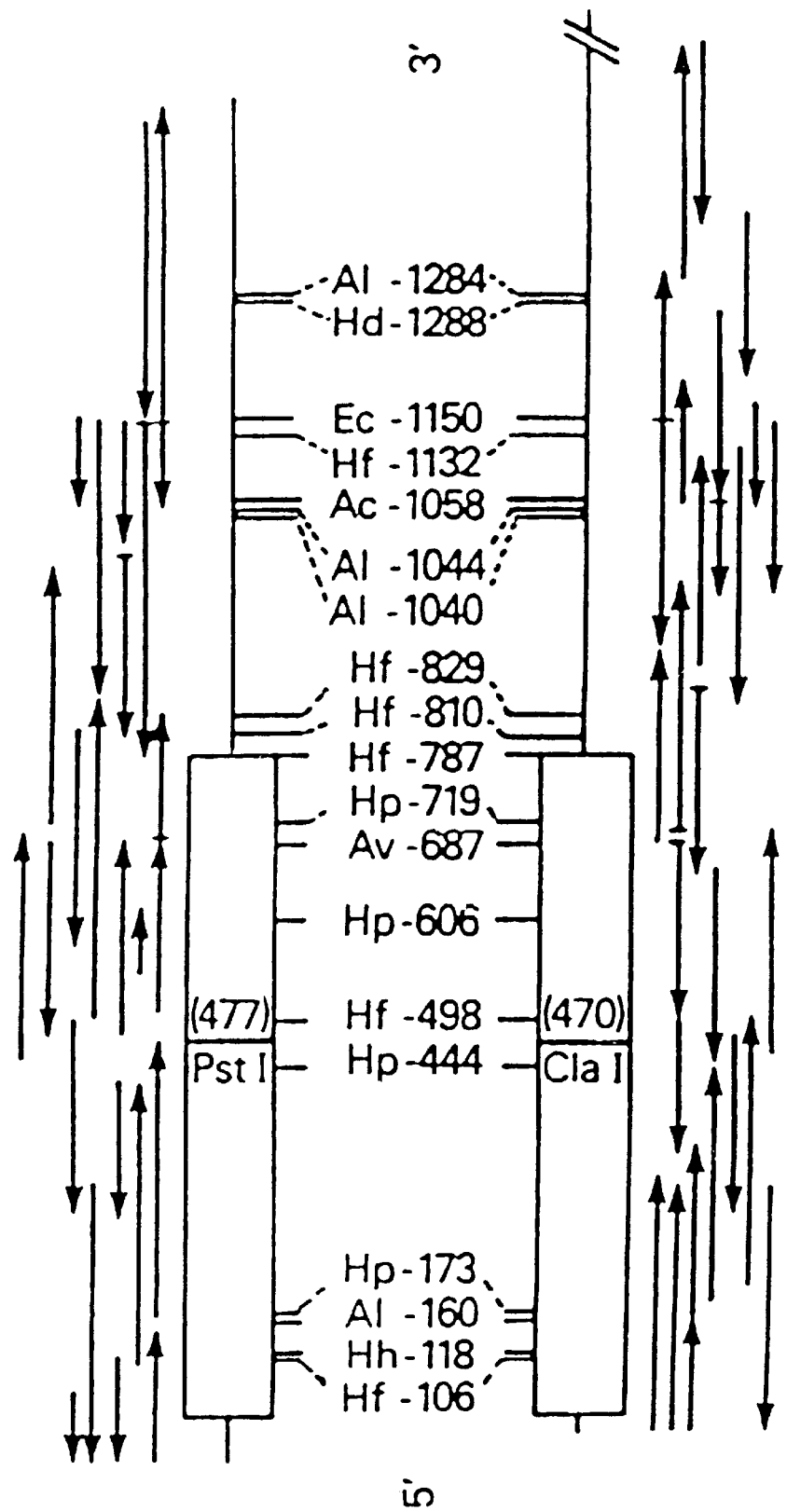

FIG. 6A

```
ACGTTTCTGT GTAACAATAT CTTTTATTCC TGGATAGTCC AATTA ATG AAA AAA     54
                                              Met Lys Lys
                                               -3

ATG GAC ACA GAA AAT AAG AGC AGA GCA GAT CTT GCT CTC CCA AAC CCA   102
Met Asp Thr Glu Asn Lys Ser Arg Ala Asp Leu Ala Leu Pro Asn Pro
 1                5                 10                 15

CAA GAA TCC CCC AGC GCA CCT GAC ATT GAA CTC TTG GAA GCG TCC CCT   150
Gln Glu Ser Pro Ser Ala Pro Asp Ile Glu Leu Leu Glu Ala Ser Pro
                 20                 25                 30

CCT GCA AAA GCT CTA CCA GAG AAG CCA GCC TCA CCC CCA CAG CAG       198
Pro Ala Lys Ala Leu Pro Glu Lys Pro Ala Ser Pro Pro Gln Gln
                 35                 40                 45
```

FIG. 6B

```
ACA TGG CAG TCA TTT TTG AAG AAA GAG TTG GAG TTC CTG GGC GTA ACC      246
Thr Trp Gln Ser Phe Leu Lys Lys Glu Leu Glu Phe Leu Gly Val Thr
         50                      55                      60

CAA GTT CTG GTT GGT TTG ATA TGC CTT TGT TTT GGA ACA GTT GTC TGC      294
Gln Val Leu Val Gly Leu Ile Cys Leu Cys Phe Gly Thr Val Val Cys
 65                      70                      75              80

TCC ACA CTC CAG ACT TCA GAC TTT GAC GAC GAA GTG CTT TTA TTA TAT      342
Ser Thr Leu Gln Thr Ser Asp Phe Asp Asp Glu Val Leu Leu Leu Tyr
         85                      90                      95

AGA GCA GGC TAC CCA TTC TGG GGT GCA GTG CTG TTT GTT TTG TCT GGA      390
Arg Ala Gly Tyr Pro Phe Trp Gly Ala Val Leu Phe Val Leu Ser Gly
            100                     105                     110

TTT TTG TCA ATT ATG TCC GAA AGG AAA AAC ACA CTG TAT CTG GTG AGA      438
Phe Leu Ser Ile Met Ser Glu Arg Lys Asn Thr Leu Tyr Leu Val Arg
            115                     120                     125

GGC AGC CTG GGA GCA AAC ATT GTC AGC ATC GCT GCA GGC TTG GGG          486
Gly Ser Leu Gly Ala Asn Ile Val Ser Ile Ala Ala Gly Leu Gly
            130                     135                     140

ATC GCC ATA TTG ATT CTC AAT CTG AGC AAC AAC TCC GCT TAT ATG AAC      534
Ile Ala Ile Leu Ile Leu Asn Leu Ser Asn Asn Ser Ala Tyr Met Asn
            145                     150                     155             160
```

FIG. 6C

```
TAC TGC AAG GAT ATA ACC GAA GAC GAT GGT TGC TTC GTG ACT TCT TTC    582
Tyr Cys Lys Asp Ile Thr Glu Asp Asp Gly Cys Phe Val Thr Ser Phe
            165                 170                 175

ATC ACA GAA CTG GTG TTG ATG TTG CTG TTT CTC ACC ATC CTG GCC TTT    630
Ile Thr Glu Leu Val Leu Met Leu Leu Phe Leu Thr Ile Leu Ala Phe
        180                 185                 190

TGC AGT GCC GTG CTG CTC ATT ATC ATC TAT AGG ATT GGA CAA GAA TTT GAG    678
Cys Ser Ala Val Leu Leu Ile Ile Tyr Arg Ile Gly Gln Glu Phe Glu
    195                 200                 205

CGT AGT AAG GTC CCC GAT GAC CGT CTC TAT GAA GAA TTA CAT GTG TAT    726
Arg Ser Lys Val Pro Asp Asp Arg<Leu Tyr Glu Glu Leu His Val Tyr
210                 215                 220

TCA CCA ATT TAC AGT GCG TTG GAA GAC ACA AGG GAA GCG TCC GCA CCA    774
Ser Pro Ile Tyr Ser Ala Leu Glu Asp Thr Arg>Glu Ala Ser Ala Pro
225                 230                 235                 240

GTG GTT TCA TAAGAATCAA GGGGCCAGGA CAATCTGATT CCAGTCTAGT    823
Val Val Ser>
```

FIG. 6D

```
CTTGAGAGTC GATCTTTTTG CAACATTATG GCAACATTTC TGTTTCCTCC GCACTCTATC   883
AACTTTTCAA TTGGATTGTT CTGTAGATAC CCCTGTTTCA GTTATGATGC CTCTGGTCTT   943
TAATTATCTC CCTTTTGTG GATATCGTTC AATCCAGTTT TCTTGTTTTG TGTCACAGTC   1003
TCACATACAA CCTTTCTGGA AAGTCATCAA AAACAAGCTA GCTTTTATTG CATGTCTACT   1063
TTCATGAACA AAAGGAAGGA GGAGTTATTT TGAGAGTTTA ACTAAACTTA GATAATCAGG   1123
TAATATTTGA CTCTTAGTTC ATTTTAGAAT TCTCAACAAT ACTTGTGCAT GATATATGCC   1183
CACCATATCA AGCCTCTAT ATATATTTAA TATGGTATTT ACTTTTCTAT GTAGATAGAT   1243
TTTCCACCCT CAATAATAAT GGGTTTTTCA GAGACATAAA GCTTTATGAA AAGACACATA   1303
```

FIG. 6E

```
TTATCTAATT CATGGGTATA TTCACTAATA CAGTTGTTGC TCAGTGGTGT TTACTACTTG    1363
GTGGGTAGTA GGTAATAGAG AACATTATTA AATCATTCAG TGTAGTGAGA TGCATAGGTA    1423
AAATCAGGGA CACTGTGAGT GTGTATATCT TTTGGTAAGA CATGTGTGAA AATGAAGAAT    1483
AAACTGATGA AGACTTGAGC TGGAAAGTAG TCAATGGGAA TGACAAGAAA TGATTGTGTA    1543
TAACACTTGT AGATAAATAA CTACCAACAA TTGGTAGAGA TTGCCATGTA TGCCTAAAAT    1603
CTCCCAGCCC AAGGCCAGCC TCTGTTACAC AGTGAGTTAG AGGCCAGTCT GGGCTACACA    1663
AGATCATACA TCAAAGGACG AAAGAAGATG TTGGTTCAAA CTGTTAACAC AGTAAGGAT    1723
ATTTAAACAA ACAGAAGTTT GACTGATATA TTGAGTGCTT GAGTTTTTAA TAAAACTGAA    1783
TGAATAACAT TGCGGGGGAG GGGAGCAGTG ATGCAGAAGT CTGGATGATG GAGGAGTAGC    1843
AGAATCAGAT GAAACATTGA AACGTATTTC CAGACTTTTG TTCTGAGATG GTTATAAGAG    1903
```

FIG. 6F

```
CAATCACCAT TAAATGAAGA AGGTCAAGAC ACCAAAAGAA TTATTTTCAG ATAGAATTAA    1963
GACAGTCAAA ATCCACATGC CTATACTTAG AAGGTGAAGT AAGGATCAAA AGTAGAAAGC    2023
CTAACGATTA GTTGGAAAAG CATATTACGT TAGGCAGCAG ATGTCTATAG TGGAGAAAAG    2083
TTAAACAAGG AGAAATAATG AACCACCAGA GACTCTACAT GTTGGTTTGG GAAATAAGAG    2143
AAAATAGCAA TTCTAAACGA ATGCAAACTC TGAAGAAGCA TTTCCCAAAG GGTGTGGGCA    2203
GAGGACCAGA ACATTTGCAA ATGTACCTAG AGAGCAAACC TGAATAGGAG GTAAAATGGG    2263
GGAAAAGCAG CTAAGAAAAT GATTTGTTG CTGTTATTTA GATTTAAAA GAAACAAAAA      2323
GAGTCATTAA AAATCTGTTT GCTGGGATCA GTTATTGTGT TCTCTGTGTA TGTCCAAAGT    2383
ACAGGTAACT TTTCTAAATC TTCCTGTAAG GCTCACCCTCA TATGTCTCTT CACATAGCCA   2443
CACCCTTGAT TCACAGTTAC TCTACCACAG TAGTAAACTG TGCTTGTGGT CTCCCTTATG    2503
TATCTTCACT AGTGTTTATA AAATAAATCA GAATTATTTA AA                       2545
```

FIG. 6G

```
GTG AGA ACA TAT CTG TAATTGTTTC TGAAATGATG CTAACCAGAG ATTTATTTT          55
Val Arg Thr Tyr Leu
  1               5

AATCAAAGAC AACTAATTTT CTTTTAATCA AGTGCTTATC TCTAGCCTTT CAATAATATC      115

TACAGTTCTT CATTTATATG CACATAGCCA TCTATAAATG TAGTTCCAA AGCACTCTCT      175

ACATATACTC ATTAACAAGA GCAAATACAC TCACCACAGT TAACTATGGT TTAACCCATT     235

ACTATACTTT TATTGACTGA AAACCTTGAG ACTGTACAAA AAAAAAAAA A               286
```

FIG. 9

```
AGCGCTGCAGCCCCGCCCAGG ATG ATC CCA GCG GTG ATC TTG TTC          46
                      M   I   P   A   V   I   L   F          -11

TTG CTC CTT TTG GTG GAA GAA GCA GCT GCC CTA GGA GAG CCG CAG    91
 L   L   L   L   V   E   E   A   A   A   L   G   E   P   Q     5
                                        -1  +1

CTC TGC TAT ATC CTG GAT GCC ATC CTG TTT TTG TAT GGT ATT GTC   136
 L   C   Y   I   L   D   A   I   L   F   L   Y   G   I   V    20

CTT ACC CTG CTC TAC TGT CGA CTC AAG ATC CAG GTC CGA AAG GCA   181
 L   T   L   L   Y   C   R   L   K  (I   Q   V   R)  K   A    35

GAC ATA GCC AGC CGT GAG AAA TCA GAT GCT GTC TAC ACG GGC CTG   226
 D   I   A   S   R  (E   K   S   D   A   V   Y)  T   G   L    50

AAC ACC CGG AAC CAG GAG ACA TAT GAG ACT CTG AAA CAT GAG AAA   271
 N   T   R  (N   Q   E   T   Y   E   T   L   K)  H   E   K    65

CCA CCC CAA TAG CTTTACAACACGTGTTCTCAGCTGCATTCCTTTTCCGCTTTTA   326
 P   P   Q   -                                                 68

ATTCTCCTCGCCCTCATGATTGACGTGGCTGTGCTACCTCCGTGCTTCTGGAACTAG    385
CTGACCTTATTCCCAGAACCATGCTAGGCTCTAAATCAATGTCCCATATCCACCAAAG    444
ACTTACTCACTGACATTCTCTCCCATCCTCCTTTGCTTCCTCATTCCTCCTTTCCTTCC   503
CTGATCCTCTCTGTCTCACTAAACAATGGGAAGGATTACCCCCCAATAAAGCTGCCAGA   562
GATCACGCTCAAAAAAAAAAAA                                        586
```

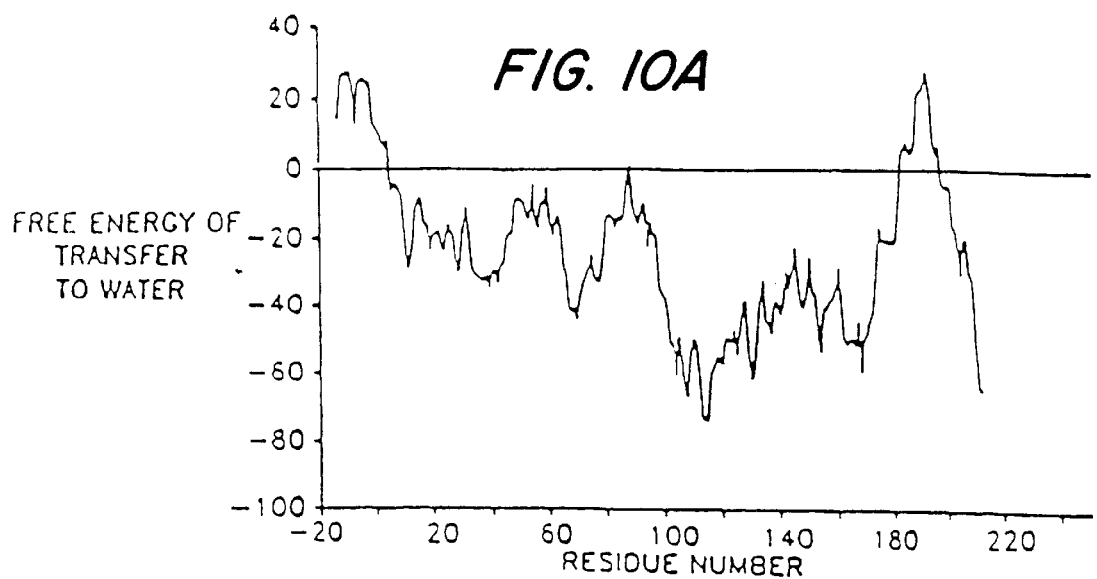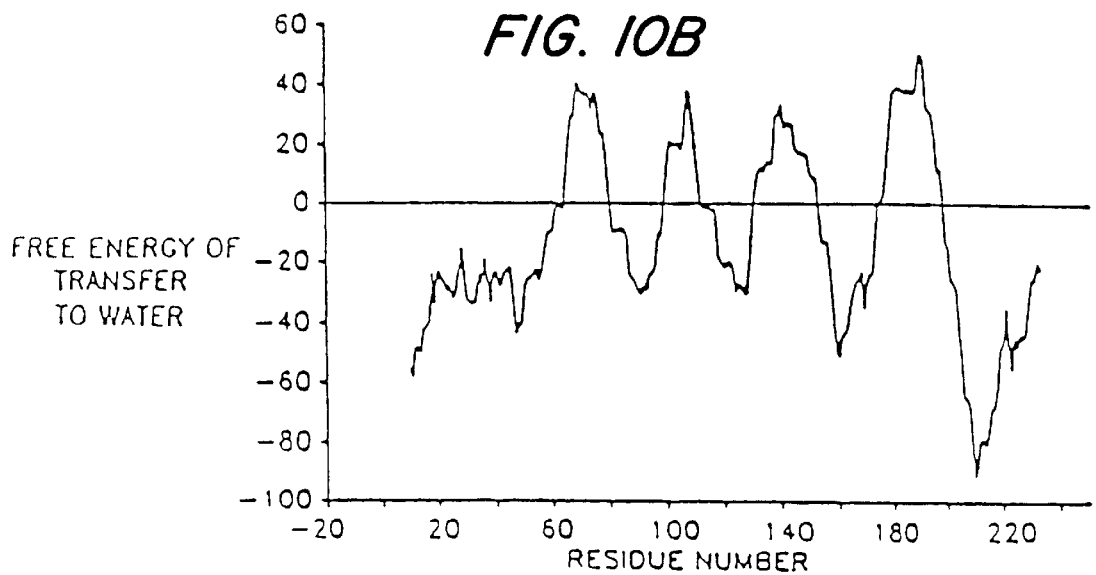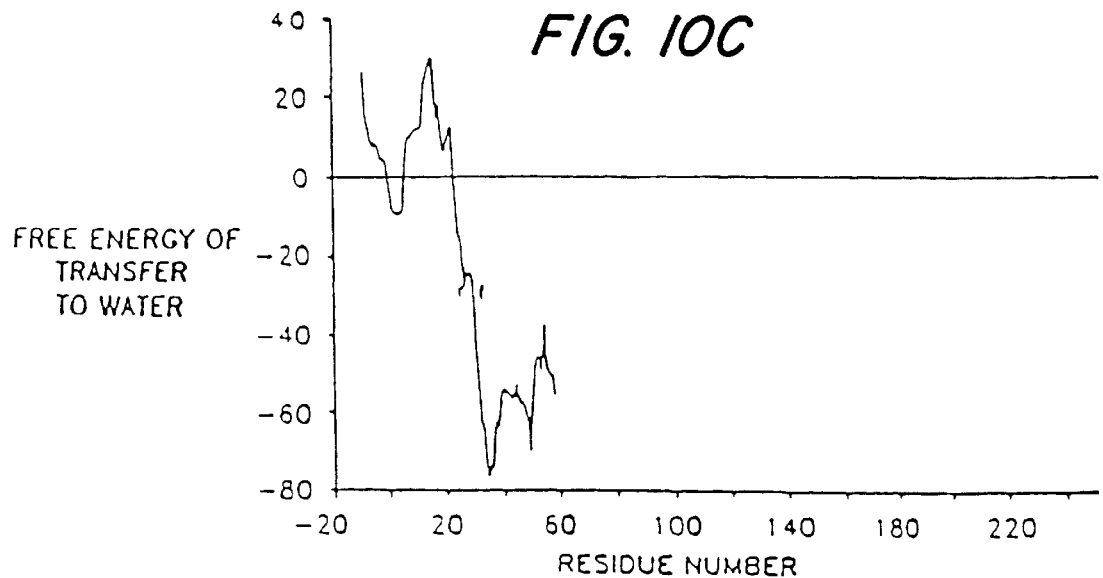

TO FIG. 12B

ISOLATION AND CHARACTERIZATION OF CDNAS CODING FOR THE α, β, AND γ SUBUNITS OF THE HIGH-AFFINITY RECEPTOR FOR IMMUNOGLOBULIN E

This application is a continuation in part of application Ser. No. 07/259,065, filed Oct. 18, 1988 abandoned, which is a continuation-in-part of U.S. patent application Ser. No. 07/160,457, filed Feb. 24, 1988 now U.S. Pat. No. 5,639,660, and U.S. patent application Ser. No. 07/240,692, filed Sep. 6, 1988 abandoned, the contents of all of which are incorporated herein by reference.

BACKGROUND OF THE INVENTION

FIELD OF THE INVENTION

The present invention relates to DNA segments encoding the α, β, and γ subunits of the high affinity receptor for immunoglobulin E (IgE). The invention further relates to a method of producing the receptor by expressing DNA encoding its α, β, and γ subunits in a host cell simultaneously.

BACKGROUND OF THE INVENTION

Receptors that bind the Fc region of immunoglobulins ("Fc receptors") mediate immunoglobulin transport across membranes, stimulate a variety of cellular activities induced by antigen-antibody complexes, and possibly regulate the biosynthesis of antibodies. Three of the receptors (the receptor for polymeric immunoglobulin (Mostov et al. (1984) Nature (London) 308:37–43), the Fc receptors on macrophages and lymphocytes (Ravetch et al. (1986) Science 234:718–725), and the high-affinity Fc, receptor on mast cells and basophils (Kinet et al. (1987) Biochemistry 26:4605–4610; Shimizu et al. (1988) Proc. Natl. Acad. Sci. USA 85:1907–1911; Kochan et al. (1988) Nucleic Acids Res. 16:3584) share a common feature: their immunoglobulin-binding portion contains two or more immunoglobulin-like domains.

The receptor with high affinity for IgE ($Fc_\epsilon RI$) is found exclusively on mast cells, basophils and related cells. Aggregation of IgE occupied $Fc_\epsilon RI$ by antigen triggers both the release of preformed mediators such as histamine and serotonin, as well as stimulation of the synthesis of leukotrienes. It is the release of these mediators that results in the allergic condition.

The most thoroughly characterized $Fc_\epsilon RI$ is that of the rat basophilic leukemia (FEL) cell line. It consists of three different subunits: (1) a 40–50 Kilodalton (Kd) glycoprotein alpha chain which contains the binding site for IgE, (2) a single 33 Kd beta chain and (3) two 7–9 Kd disulfide linked gamma chains (H. Metzger et al, Ann. Rev. Immunol. 4:419–470 (1986)).

Complementary DNA (cDNA) for the rat α subunit has recently been isolated (J.-P. Kinet et al, Biochemistry 26:4605–4610 (1987)). However, previously there has been no disclosure of the isolation and characterization of the β and γ subunits or of a cDNA of the human α subunit; nor has it been possible to express IgE-binding by transfected cells (J.-P. Kinet et al, Biochemistry 26:4605–4610 (1987); A. Shimizu et al, Proc. Natl. Acad. Sci. USA 85:1907–1911 (1988)).

The present invention provides in one embodiment, a cDNA clone for the alpha subunit of the human $Fc_\epsilon RI$. The invention further provides, in further embodiments, cDNA clones for the β and γ subunits of $Fc_\epsilon RI$. The invention still further provides a method of producing the $Fc_\epsilon RI$ receptor.

SUMMARY OF THE INVENTION

It is a general object of this invention to provide DNA segments encoding $Fc_\epsilon RI$.

It is a specific object of this invention to provide DNA segments of the α, β, and γ subunits of $Fc_\epsilon RI$.

It is a further object of the invention to provide polypeptides corresponding to the α, β, and γ subunits of $Fc_\epsilon RI$.

It is another object of the invention to provide a recombinant DNA molecule comprising a vector and a DNA segment encoding the α, β, or γ subunits of $Fc_\epsilon RI$.

It is a further object of the invention to provide a cell that contains the above-described recombinant DNA molecule.

It is another object of the invention to provide a method of producing polypeptides having amino acid sequences corresponding to the α, β, and γ subunits of $Fc_\epsilon RI$.

It is a further object of the invention to provide a method of producing a functional $Fc_\epsilon RI$ receptor.

Further objects and advantages of the present invention will be clear from the description that follows.

In one embodiment, the present invention relates to DNA segments that code for polypeptides having amino acid sequences corresponding to the α, β, and γ subunits of $Fc_\epsilon RI$.

In another embodiment, the present invention relates to polypeptides having amino acid sequences corresponding to the α, β, and γ subunits of $Fc_\epsilon RI$.

In a further embodiment, the present invention relates to recombinant DNA molecules comprising a vector and a DNA segment that codes for a polypeptide having an amino acid sequence corresponding to the α, β, or γ subunits of $Fc_\epsilon RI$.

In yet another embodiment, the present invention relates to a cell that contains the above described recombinant DNA molecule.

In a further embodiment, the present invention relates to a method of producing polypeptides having amino acid sequences corresponding to the α, β, and γ subunits of $Fc_\epsilon RI$.

In another embodiment, the present invention relates to a method of producing a functional $Fc_\epsilon RI$ receptor comprising introducing into a host cell DNA segments encoding the α, β, and γ subunits of $Fc_\epsilon RI$; and effecting expression of said DNA segments under conditions such that said receptor is formed. Expression of the receptor on the surface of COS 7 cells is achieved by the present invention when the cDNA for all three subunits of $Fc_\epsilon RI$ are simultaneously cotransfected. This success in expression of IgE binding permits detailed analysis of the IgE-receptor interaction and thus enables the development of therapeutically effective inhibitors.

BRIEF DESCRIPTION OF THE DRAWINGS

FIG. 1. The nucleotide sequence and predicted amino acid sequence of human $Fc_\epsilon RI$ alpha cDNA are shown.

FIG. 2. The amino acid sequence homology of rat $Fc_\epsilon RI$ alpha subunit (R), human $Fc_\epsilon RI$ alpha subunit (A), and mouse $Fc_\epsilon RI$ alpha subunit (M) are shown. The regions of identity between the three are boxed. The number one position corresponds to the site of the predicted mature N-terminus of each protein.

FIG. 5. Restriction maps for β cDNAs and strategy by which they were sequenced. The open rectangle indicates the sequence predicted to code for the β subunit; the lines indicate the 5' and 3' untranslated regions. The upper scheme shows the 1.5 kilobase (kb) clone containing a Pst I cleavage site. The lower scheme shows a 2.4-kb clone containing a ClaI cleavage site. The 3' region of the latter has been truncated as indicated by the slashes. Its untranslated portion was sequenced as completely as the rest of the clone. Restriction sites are indicated by vertical bars: Hf, HinfI; Hh, Hha I; Al, Alu I; Hp, Hph I; Av, Ava II; Ac, Acc I; Ec, EcoRI; Hd, HindIII. The horizontal arrows show the direction and extent of sequencing by the dideoxynucleotide chain-termination method.

FIG. 6. (A)(2)–(6) Nucleotide and deduced amino acid sequences of the cDNA coding for the β subunit. Beginning at the arrowhead (▼), an alternative sequence FIG. 6B was observed in six clones. The putative transmembrane domains are underlined. The tryptic peptides of the β subunit, from which the amino acid sequences were determined directly, are bracked (<>). A putative poly(A) signal near the end is underlined. FIG. 6B Continuation of the nucleotide sequence of the deleted form of β cDNA, 3' to the junction indicated in A (▼).

FIG. 9. Nucleotide sequence of the γ subunit of rat Fc$_\epsilon$RI and the amino acid sequence that it predicts. The putative transmembrane domain is underlined. Amino acid resides are numbered starting with the first residue of the mature protein. Residues 5' to residue 1 have negative numbers and include the residues encoding a putative signal peptide according to the criteria of G. von Heijne (Nucleic Acids Res. 14:4683–4690 (1986)). The N-terminal and C-terminal cleavage sites are indicated by an arrow. The four tryptic peptides which were covered and sequenced are bracketed. An asterisk denotes an ambiguous residue in the sequence of the first tryptic peptide.

FIG. 10. Hydropathicity plot of predicted sequences of Fc$_\epsilon$RI: α subunit (panel A), β subunit (panel B) and γ subunit (panel C). The hydropathicity scale is according to Engelman et al (Ann. Rev. Biophys. Biophys. Chem. 15:321–353 (1986)). The summed hydropathicity values for the 20 amino acids in successive "windows" is plotted at the position corresponding to the tenth residue.

DETAILED DESCRIPTION OF THE INVENTION

Figure 3:
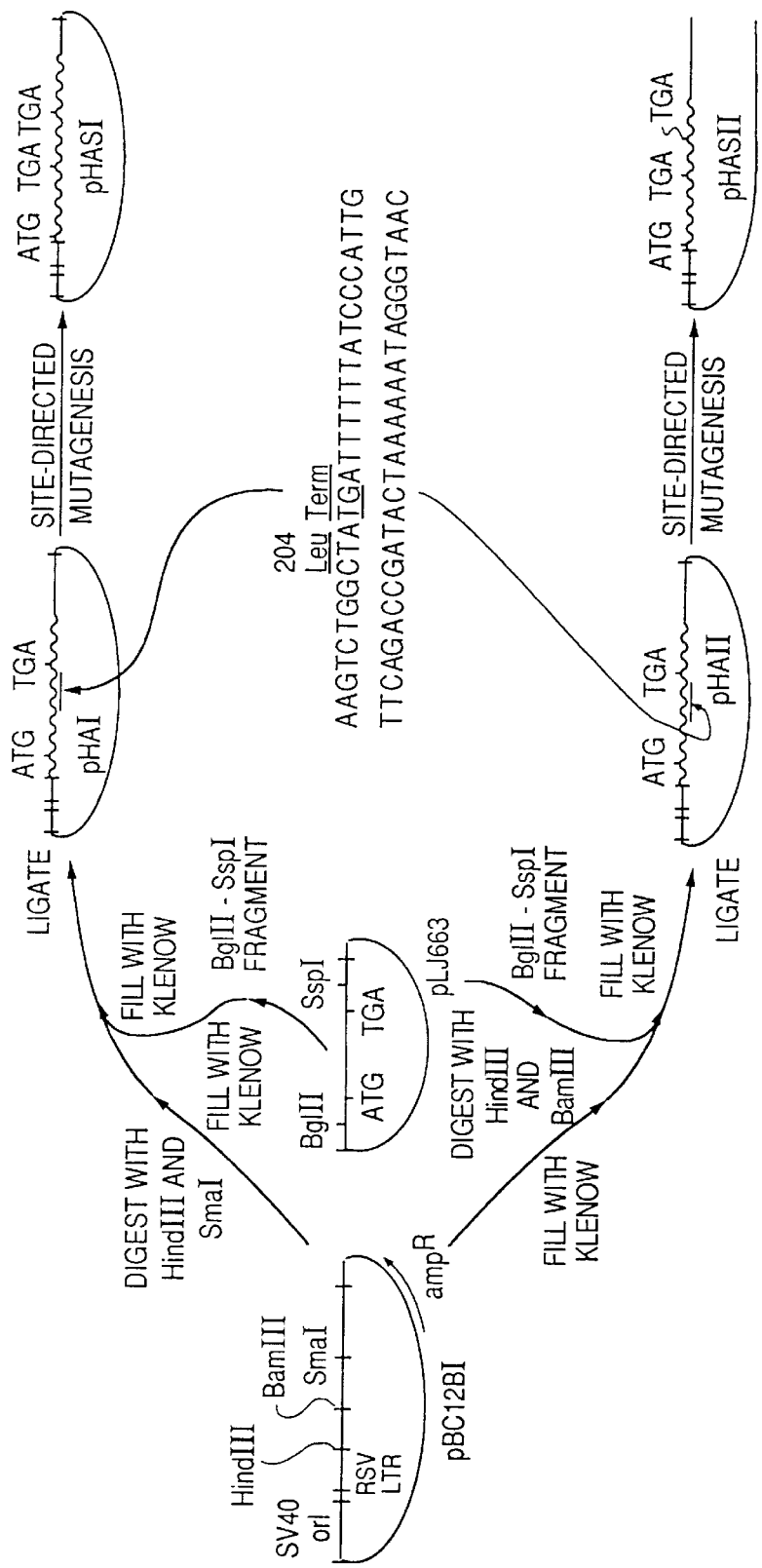
FIG. 3. A flow chart showing the construction of eukaryotic expression vectors which direct the synthesis of a complete biologically active $Fc_\epsilon RI$ alpha chain (pHAI, pHAII) or a soluble, secreted, biologically active Fc$_\epsilon$RI alpha chain (pHASI, pHASII) is presented.

The present invention relates, in part, to DNA sequences which code for polypeptides corresponding to the subunits of human $Fc_\epsilon RI$.

More specifically, the present invention relates to DNA segments (for example, cDNA molecules) coding for polypeptides having amino acid sequences corresponding to the α, β, and γ subunits of $Fc_\epsilon RI$. In one embodiment, the DNA segments have the sequence shown in FIGS. 1, 6, or 9, or allelic or species variation thereof, or a unique portion of such a sequence (unique portion being defined herein as at least 15–18 bases). In another embodiment, the DNA segments encode the amino acid sequence shown in FIGS. 1, 6, or 9, or allelic or species variation thereof, or a unique portion of such a sequence (unique portion being defined herein as at least 5–6 amino acids).

In another embodiment, the present invention relates to polypeptides having amino acid sequences corresponding to the α, β, and γ subunits of $Fc_\epsilon RI$. In one preferred embodiment, the polypeptides have amino acid sequences as shown in FIGS. 1, 6, and 9, or allelic or species variations thereof, or a unique portion of such sequences (unique portion being defined herein as at least 5–6 amino acids).

In another embodiment, the present invention relates to a recombinant DNA molecule comprising a vector (for example—plasmid or viral vector) and a DNA segment coding for a polypeptide corresponding to the α, β, or γ subunit of $Fc_\epsilon RI$, as described above. In a preferred embodiment, the encoding segment is present in the vector operably linked to a promoter.

In further embodiment, the present invention relates to a cell containing the above described recombinant DNA molecule. Suitable host cells include procaryotes (such as bacteria, including *E. coli*) and both lower eucaryotes (for example yeast) and higher eucaryotes (for example, mammalian cells). Introduction of the recombinant molecule into the host cell can be affected using methods known in the art.

In another embodiment, the present invention relates to a method of producing the above described polypeptides, comprising culturing the above described host cells under conditions such that said polypeptide is produced, and isolating said polypeptide.

In a further embodiment, the present invention relates to a method of producing a functional $Fc_\epsilon RI$ receptor comprising introducing into a host cell DNA segments encoding the α, β, and γ subunits of $Fc_\epsilon RI$; and effecting expression of said segments under conditions such that said receptor is formed.

The DNA sequences and polypeptides according to this invention exhibit a number of utilities including but not limited to:

1. Utilizing the polypeptide or a fragment thereof as an antagonist to prevent allergic response, or as a reagent in a drug screening assay.
2. Utilizing the polypeptide as a therapeutic.
3. Utilizing the polypeptide for monitoring IgE levels in patients.
4. Utilizing the DNA sequence to synthesize polypeptides which will be used for the above purposes.
5. Utilizing the DNA sequences to synthesize cDNA sequences to construct DNA useful in diagnostic assays.

The present invention will be illustrated in further detail in the following examples. These examples are included for illustrative purposes and should not be considered to limit the present invention.

EXAMPLE 1

Isolation of cDNA Clones for the Alpha Subunit of Human $Fc_\epsilon RI$

RNA was extracted from KUB12 cells as described by Kishi, *Leukemia Research*, 9,381 (1985) by the guanidium isothiocyanate procedure of Chirgwin, et al., *Biochemistry*, 18,5294 (1979) and poly(A) mRNA was isolated by oligo-dt chromatography according to the methods of Aviv, et al., *P.N.A.S. U.S.A.*, 69,1408 (1972). cDNA synthesis was performed as previously described Kinet, et al., *Biochemistry*, 26,2569 (1987). The resulting cDNA molecules were ligated to EcoRI linkers, digested with the restriction enzyme EcoRI, size fractioned and ligated to λgt11 EcoRI arms as set forth in Young et al., *Science*, 222,778 (1983). The cDNA insert containing λgt11 DNA as packaged into bacteriophage lambda particles and amplified on Y1090. A total of $1.2 \times 10^6$ independent cDNA clones were obtained. The cDNA library was plated onto Y1090 on 150 mm² plates ($10^5$ per plate) and transferred to nitrocellular filters. The cDNA library filters were screened by in situ hybridization using a nick translated cDNA fragment as in Kochan, et al., *Cell*, 44,689 (1986). The cDNA fragment was obtained from the rat $Fc_\epsilon RI$ alpha cDNA corresponding to nucleotides 119–781. Positive plaques were identified, purified and the cDNA inserts were subcloned, using standard techniques, into the PGEM vectors (Promega Biotech, Madison, Wis.). The cDNA insert was mapped by restriction enzyme analysis, subcloned into derivatives of pGEM and sequenced using the dideoxynucleotide method of Sanger et al., *P.N.A.S.*, 74,5463 (1977) following the GemSeq double strand DNA sequencing system protocol from Promega Biotech (Madison, Wis.). The DNA sequence was determined for both strands of the cDNA clone pLJ663 (nucleotides 1–1151) and for 300 bp of each end of clone pLJ 587 (nucleotides 658–1198). No discrepancy in DNA sequence between the two cDNA clones was observed.

Figure 2:
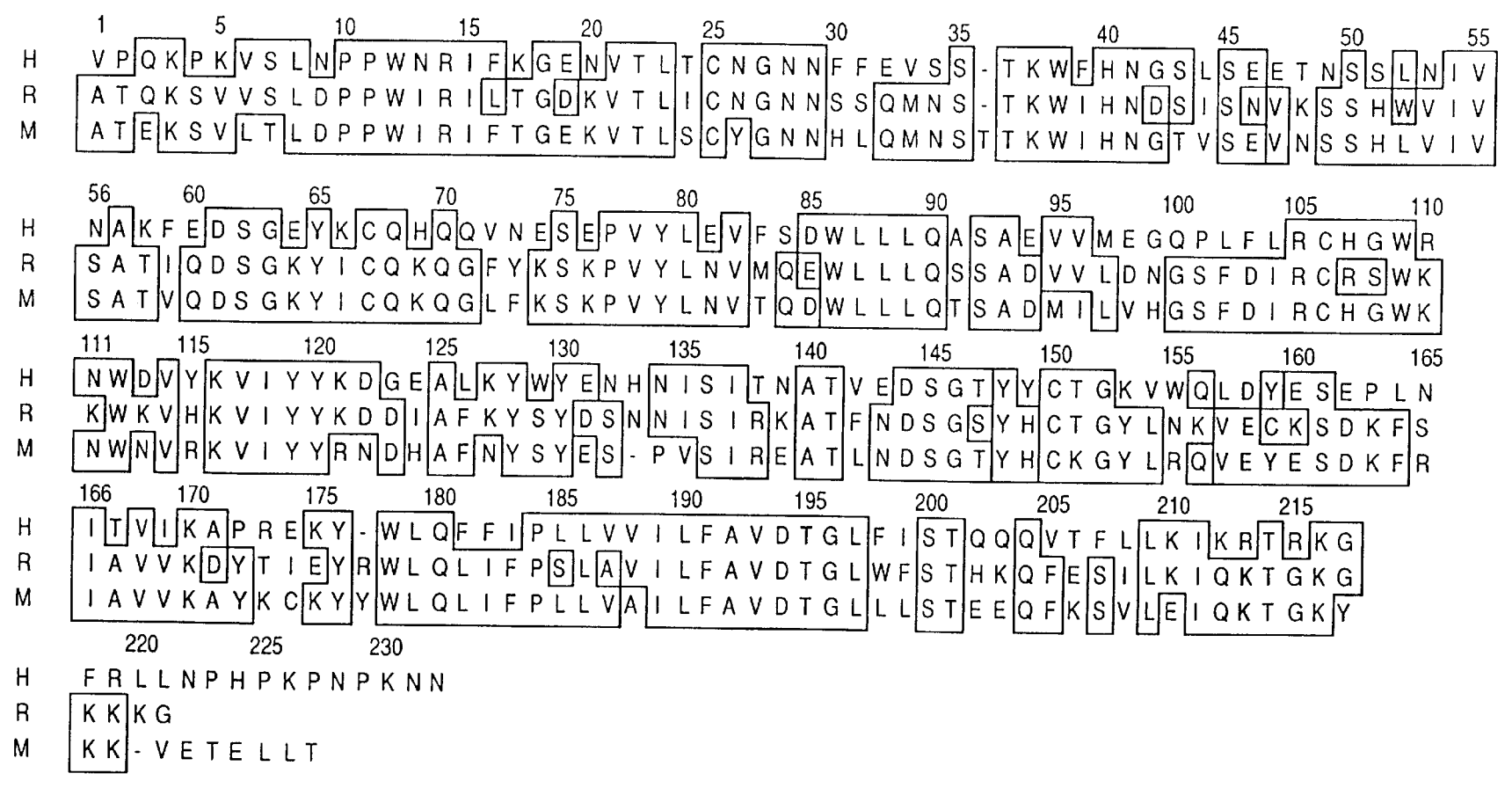

The sequence for the human $Fc_\epsilon RI$ alpha cDNA is presented in FIG. 1. The predicted amino acid sequence for the human $Fc_\epsilon RI$ alpha polypeptide is shown below the nucleotide sequence, beginning with methionine at nucleotide 107–109 and ending with asparagine at nucleotide 875–877. The site of the predicted mature N-terminus was determined to be valine at nucleotide 182–184 according to the rules set forth by von Heijne, *Eur. Journal of Biochem*; 137,17; and *Nucleic Acid Research*, 14,4683 (1986). This predicts a 25 amino acid signal peptide. The rest of the cDNA sequence suggests that the human $Fc_\epsilon RI$ alpha chain contains a 179–204) with 2 homologous domains (14 out of 25 residues are identical; residues 80–104 and 163–190), a 20-residue transmembrane segment (residues 205–224) and a 33 residue cytoplasmic domain containing 8 basic amino acids. Overall, there is 49% identity between the human and rat $Fc_\epsilon RI$ alpha sequences, and 37% identity between the human $Fc_\epsilon RI$ alpha and mouse FcGR alpha (FIG. 2). The greatest level of homology is within the transmembrane region where 9 amino acids surrounding the common aspartic acid residue are identical.

EXAMPLE 2

Expression of the Human FcϵRI Alpha Complete and Soluble Forms in Eukaryotic Cells Using the recombinant cDNA clone for the human $Fc_\epsilon RI$ alpha chain, it is possible to introduce these coding sequences into an appropriate eukaryotic expression vector to direct the synthesis of large amounts of both a complete and soluble form of the alpha chain. For surface expression it may necessary that the alpha subunit be complexed with the beta or gamma subunit whereas for the eukaryotic expression of the secreted form of the alpha subunit this may not be necessary. An appropriate vector for the purpose is pBC12BI which has previously been described in Cullen, (1987) *Methods in Enzymology* 152, Academic Press, 684. Construction of expression vectors coding for the complete alpha chain can be isolated as follows (FIG. 3): A unique BglII-SspI fragment (nucleotides 65–898) is isolated from pLJ663, the BglII end is filled in with DNA polymerase I Klenow fragment and ligated into pBC12BI which has been restricted with either HindIII-BamHI or HindIII-SmaI (the ends are made blunt by filling in with DNA polymerase I Klenow fragment). The reason for attempting two different constructions is that the former contains a 3' intron while the latter does not. The presence or absence of introns may affect the levels of the alpha protein which are synthesized in cells transfected by these vectors. Construction of expression vectors coding for the soluble form of the alpha chain would be accomplished by introducing a termination codon at nucleotides 719–721 of the coding region in the alpha chain of the expression vectors noted above (pHAI, pHAII, FIG. 3). This would remove the putative transmembrane and cytoplasmic regions resulting in the synthesis of a secreted soluble form of the human alpha chain. Introduction of a termination codon is accomplished by oligonucleotide-directed site specific mutagenesis as outlined by Morinaga et al., *Bio. Tech.*, 2, 636 (1984). The sequence of the oligonucleotide will be 5' AAGTACTGGCTATGATTTTTTATC-CCATTG 3'. The resulting expression vectors are pHASI and pHASII (FIG. 3) and these will direct the synthesis of a truncated alpha protein corresponding to amino acids 1–204. Expression of this protein in eukaryotic cells will result in synthesis of a mature, IgE binding protein encompassing amino acid residues 26–204.

The expression vectors are then introduced into suitable eukaryotic cells such as CHO or COS by standard techniques such as those set forth in Cullen, (1987), *Methods in Enzymology*, Academic Press, NY 152:684, in the presence of a selectable marker such as G418 or Methotrexate resistance. The selectable marker for Methotrexate resistance has an added advantage, since the levels of expression can be amplified by introducing the cells to higher levels of drugs. The synthesis of protein is monitored by demonstrating the ability of human IgE (or rat IgE) to bind to these cells (in the case of the complete alpha chain), or in the case of the soluble form of the alpha chain, to demonstrate that the protein secreted from these cells has the ability to bind IgE in the presence or absence of the beta.

EXAMPLE 3

Figure 4:
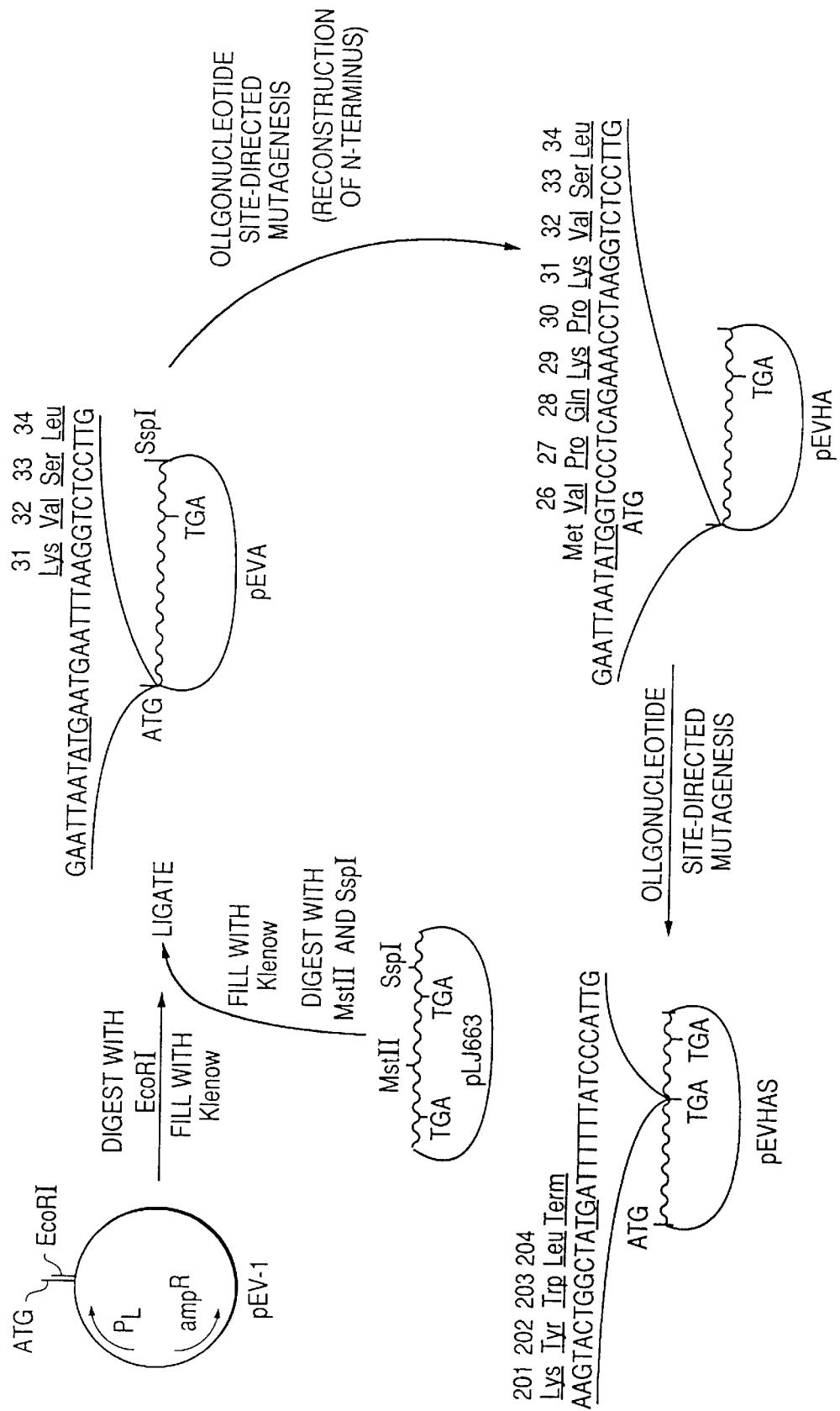
FIG. 4. A flow chart showing the construction of a prokaryotic expression vector which directs the synthesis of a soluble biologically active Fc$_\epsilon$RI alpha chain (which consists of amino acid residues 26–204) is presented.

Expression of the Human $Fc_\epsilon RI$ Alpha Soluble Form in Prokaryotic Cells Using the recombinant cDNA clone for the human $Fc_\epsilon RI$ alpha chain, it is possible to introduce these coding sequences into an appropriate prokaryotic expression vector to direct the synthesis of large amounts of a soluble (non-membrane bound) IgE binding polypeptide derived from the alpha chain. An appropriate vector for this purpose is pEV-1 which has been described by Crowl, et al., *Gene*, 38, 31 (1985). Construction of an expression vector coding for a soluble alpha chain can be isolated as set forth in FIG. 4: a unique MstII-SspI fragment (nucleotides 195–898 is isolated from pLJ663, the MstII end is filled in with DNA polymerase I Klenow fragment and ligated into pEV-1 which has been restricted with EcoRI, and the ends filled in with Klenow (FIG. 4, pEVA). The N-terminus of the mature alpha chain is reconstructed by oligonucleotide directed-site specific mutagenesis. The sequence of the oligonucleotide will be 5' GAATTAATATGGTCCCTCAGAAAC-CTAAGGTCTCCTTG 3'. Introduction of this sequence into the expression vector pEVA aligns the Methionine residue of the EV-1 vector next to Valine-26 (the predicted mature N-terminus of the alpha chain) followed by amino acid residues 27–204 (pEVHA, FIG. 4). Reconstruction of the soluble form $Fc_\epsilon RI$ alpha is accomplished by oligonucleotide site-directed mutagenesis. The sequence of the oligonucleotide will be 5'-AAGTACTGGCTATGATTTTTTATCCCATTG-3'. Introduction of this sequence into the expression vector, terminates polypeptide synthesis just prior to the start of the transmembrane region. The protein thus encoded by expression vector pEVHAS, should faithfully direct the synthesis of a soluble form of the alpha chain, corresponding to amino acid residues 26–204. This expression vector is then transformed into suitable hosts.

EXAMPLE 4

Isolation and Sequence Analysis of Peptides of the Beta Subunit of $Fc_\epsilon RI$ Since repeated attempts to sequence intact β chains were unsuccessful, peptides were isolated from tryptic digests. Electroeluted β subunits from polyacrylamide gels were prepared as described (Alcaraz et al. (1987) Biochemistry 26:2569–2575). Tryptic peptides were separated by high-pressure liquid chromatography and sequenced as before (Kinet et al. (1987) Biochemistry 26:4605–4610). A peptide (no. 1) isolated from an initial digest had the sequence Tyr-Glu-Glu-Leu-His-Val-Tyr-Ser-Pro-Ile-Tyr-Ser-Ala-Leu-Glu-Asp-Thr. The same peptide from later digests showed an additional leucine at the $NH_2$ terminus and an arginine at the COOH terminus. The sequences of three other peptides, each isolated in substantial yields, are indicated in a subsequent figure.

EXAMPLE 5

Cloning and Sequencing of cDNA clones of the Beta Subunit of $Fc_\epsilon RI$ RNA extracted from rat basophilic leukemia (RBL) cells by the guanidinium isothiocyanate method (Chirgwin et al. (1979) Biochemistry 18:5294–5299) was fractionated on an oligo(dT)-cellulose column (Maniatis et al. (1982) Molecular Cloning: A Laboratory Manual (Cold Spring Harbor Lab., Cold Spring Harbor, N.Y.) and used to construct a pUC-9 and a λgtll library (Maniatis et al. (1982) Molecular Cloning: A Laboratory Manual (Cold Spring Harbor Lab., Cold Spring Harbor, N.Y.; Young and Davies (1983) Proc. Natl. Acad. Sci. USA 80:1194–1198). The initial sequence obtained for peptide 1 was used to construct two 26-mer oligonucleotides of 32-fold degeneracy: 5'-GGIGA(A/G)TA(G/C)ACATGIA(A/G)(C/T)TC(C/T)TCATA-3' and 5'-GGICT(A/G)TA(G/C)ACATGIA(A/G)(C/T)TC(C/T)TCATA-3'. A λgt11 library constructed from mRNA of RBL cells was screened with 1:1 mixture of these oligonucleotides. Colonies were screened as before (Kinet et al. (1987) Biochemistry 26:4605–4610) using oligonucleotides prepared on a model 380A automated DNA synthesizer (Applied Biosystems, Foster City, Calif.). Six positive clones gave similar restriction patterns. cDNA inserts were subcloned into pGEM-4 or pGEM-3Z and the resulting double-stranded DNA was sequenced with the Gemseq/RT sequencing system according to the method recommended by the supplier (Promega Biotec, Madison, Wis.). Twenty-mer oligonucleotides, corresponding to previously sequenced regions by this method, were used as primers to generate overlapping sequences otherwise difficult to obtain. In some instances, DNA sequencing was performed using Sequenase as recommended by the supplier (United States Biochemical, Cleveland). The clone containing the longest insert was sequenced according to the strategy shown in the upper portion of FIG. 5. The sequence predicts possible starting codons at nucleotides 46–48 and 55–57, which would yield a polypeptide of 246 or 243 residues, respectively (FIG. 6A). The predicted $M_r$ of about 27,000 is some 20% less than the apparent molecular weight of β subunits when analyzed on polyacrylamide gels (Holowka and Metzger (1982) Mol. Immunol. 19:219–227). In addition, no in-frame stop codon was apparent upstream of the start codon. To rule out the possibility that the true start codon was still further 5', the cDNA library was rescreened with a restriction fragment (nucleotides 7–474) and with a synthetic oligonucleotide probe (nucleotides 3–32). Twenty-eight additional clones were isolated and their restriction patterns were examined. Twenty were similar to the original clones. Only six additional nucleotides at the 5' end (nucleotides 1–6. FIG. 6A) were identified. Early termination was found in six clones, which otherwise had the same sequence through nucleotide 375 (FIG. 6B). One 2.4-kb clone had cytidine 473 substituted with an adenine. This substitution abolishes the Pst I site and creates a new Cla I site at nucleotide 470. Also thereby, Ala-140 would become Asp-140 (FIG. 6A). Finally, one clone extended ≈350 base pairs (bp) in the 5' direction. The junction with the sequence shown in FIG. 6A was AATAAAACAAAAAAAAAAAAATG, the last two nucleotides of the newly generated ATG corresponding to nucleotides 8 and 9 of the previous sequence. It is likely that this clone simply resulted from the ligation of two independent cDNAs. Screening of the pUC-9 library revealed three clones. However, the sequence of none of these extended 5' beyond nucleotide 84.

EXAMPLE 6

RNA Transfer Blotting

RNA transfer blotting was performed under high stringency using a Pst I fragment probe (nucleotides 1–474). Thirty micrograms of total RNA was run on a 1% agarose gel containing 2% formaldehyde and blotted to nitrocellulose filters (Maniatis et al. (1982) Molecular Cloning: A Laboratory Manual (Cold Spring Harbor Lab., Cold Spring Harbor, N.Y.). The filters were hybridized with a restriction fragment of the β cDNA (nucleotides 1–474) as described (Maniatis et al. (1982) Molecular Cloning: A Laboratory Manual (Cold Spring Harbor Lab., Cold Spring Harbor, N.Y.) and washed with 15 mM NaCl/1.5 mM sodium citrate at 65° C. RBL cells yielded two major bands at ≈2.7 kb and 1.75 kb with the upper band having about twice the intensity of the lower one. A minor band 1.2 kb was also noted. Negative results were obtained with a variety of cells that do not express high-affinity IgE receptors: the rat pituitary line GH3 (American Type Culture Collection no. CCL82.1), the rat glial cell line C6 (no. CCL107), the mouse Leydig cell line I-10 (no. CCL83), and, notably, the mouse monocytic line J774 (no. T1B67) and the rat lymphoma "NTD" (Rivera et al. (1988) Mol. Immunol., in press).

EXAMPLE 7

In vitro Transcription and Translation cDNAs corresponding to the β subunit and various mutated or truncated forms thereof were subcloned into either pGEM-4 or pGEM-3Z transcription vectors (Promega Biotec). The β clone containing the Pst I site was transcribed in vitro with T7 RNA polymerase. Unlabeled RNAs were synthesized using either SP6 or T7 polymerase as recommended by the supplier. Capping reactions were performed as reported (Contreras et al. (1982) Nucleic Acids Res. 10:6353–6362). After digestion of the template with RNase-free DNase I, the RNAs were purified further by extraction with phenol/chloroform and three precipitations from ethanol. The RNA was then translated with a micrococcal nuclease-treated lysate of rabbit reticulocytes in the presence of [$^{35}$S] methionine as recommended by the supplier (Promega Biotec). The products of translation were diluted 1:1 with 20 mM detergent {3-[3-(cholamidopropyl)dimethylammonio]-1-propane sulfonate in borate-buffered saline (pH 8) containing 30 µl of aprotinin per ml, 175 µg of phenylmethyl-sulfonyl fluoride per ml, 10 µg of leupeptin per ml, and 5 µg of pepstatin per ml and immunoprecipitated with monoclonal antibodies as described (Rivera et al. (1988) Mol. Immunol., in press). The unfractionated translated material showed a major component at $M_r$≈32,000 compared to the control from which the RNA had been omitted or an alternative RNA (brome mosaic virus) had been substituted (data not shown).

The isolation of antibodies was as follows: *Escherichia coli* transformed with an expression vector containing the desired restriction fragments (Crowl et al. (1985) Gene 38:31–38; Portnoy et al. (1986) J. Biol. Chem. 261:14697–14703) were cultured and induced, and the fraction enriched for the recombinant protein was prepared as described (Portnoy et al. (1986) J. Biol. Chem. 261:14697–14703). After separation on polyacrylamide gels in sodium dodecyl sulfate (NaDodSO$_4$) the transformant-specific protein was eluted and used to immunize rabbits. Approximately 100 µg of protein was injected in complete Freund's adjuvant; this was followed by a booster injection of 25 µg of protein in incomplete adjuvant. The isolation and characterization of monoclonal anti-β antibodies mAbβ (JRK) and mAbβ(NB) (the latter, a generous gift from David Halowka, Cornell University) have been described (Rivera et al. (1988) Mol. Immunol., in press).

Figure 7A:
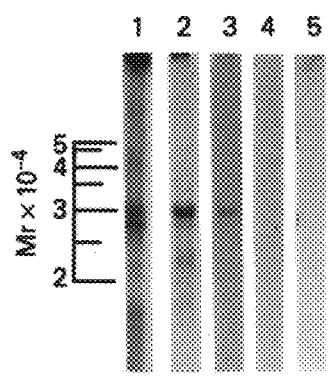
FIG. 7. Expression of cDNA coding for the β subunit. (A) Comparison of in vivo and in vitro translation products. RBL cells were grown in [$^{35}$S] cysteine containing medium. The detergent extract of the cells was precipitated with mAbβ(JRK) and, after vigorous washing, extracted with sample buffer and electrophoresed (lane 1). This experiment employed concentrations of detergent high enough to dissociate the receptor completely. A transcript from the β cDNA was treated in vitro in [$^{35}$S ]methionine-containing medium (lanes 2, 3, and 5). A control incubation contained no cDNA (lane 4). The mixtures were allowed to react with monoclonal antibodies to the β subunit after a clearing immunoprecipitation. The specific washed precipitates were dissolved in sample buffer and electrophoresed: lanes 2 and 4, mAbβ(JRK); lane 3, mAbβ(NB); lane 5, irrelevant monoclonal antibody [mAb(LB)]. An autoradiograph of the 12.5% polyacrylamide gel on which the specimens were analyzed under reducing conditions is shown. (B) Localization of one epitope to the NH$_2$-terminal peptide of the β subunit. A β cDNA-containing vector was digested with HhaI before transcription using T7 polymerase. The resulting mRNA was translated to generate an NH$_2$-terminal peptide of the β subunit (amino acid 1–21) labeled with [$^{35}$S]methionine. The mixture was allowed to react with mAbβ(JRK) (lane 1) and the irrelevant mAb(LB) (lane 2). The precipitates were analyzed on a 17% gel under nonreducing conditions. (C) Expression by E. coli of a COOH-terminal fragment of the β subunit. A HinfI fragment, containing nucleotides 499–787, was subcloned into an E. coli expression vector (Crowl et al. (1985) Gene 38:31–38) and extracts were prepared. The proteins were electrophoresed as in A and transferred to nitrocellulose paper. The latter was allowed to react sequentially with monoclonal antibody mAbβ(NB), developed with alkaline phosphatase-conjugated goat anti-mouse IgG (Fc), and developed in the usual way (Rivera et al. (1988) Mol. Immunol., in press). An enlargement of the lower half of the immunoblot is shown. Lane 1, extract from transformant without insert; lane 2, extract from transformant with insert in wrong direction; lane 3, extract from transformant with insert correctly oriented. (D) Reactivity of β subunits with polyclonal antibodies induced by E. coli-expressed HinfI fragments. Purified IgE-receptor complexes were electrophoresed, transferred to nitrocellulose paper, and allowed to react with antibodies and subsequently with an appropriate alkaline phosphatase-conjugated anti-immunoglobulin antibody. Lane 1, mAbβ (JRK); lane 2, mAbβ(NB); lane 3, immune serum to fragment A; lane 5, immune serum to fragment B; lanes 4 and 6, preimmune sera corresponding to the immune sera in lanes 3 and 5, respectively; lanes 7 and 8, second antibody only. This gel was run without molecular weight standards.
Figure 7B:
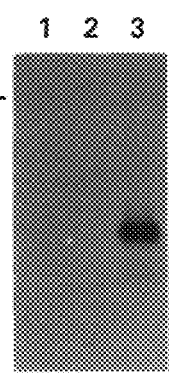

The monoclonal anti-β antibodies mAbβ(JRK) and mAbβ (NB) (Rivera et al. (1988) Mol. Immunol., in press) (FIG. 7A, lanes 2 and 3)—but not an irrelevant antibody (lane 5)-precipitated radioactive material, which on polyacrylamide gels in NaDodSO$_4$ showed a major band at $M_r$32000. This band had the identical mobility as the upper band of the doublet precipitated by mAbβ(JRK) from an extract of labeled RBL cells (lane 1). Although not seen well in the reproduction, the autoradiogram showed that the material synthesized in vitro also contained the lower molecular weight component seen the in vivo synthesized β chains. The mobility of the in vitro synthesized protein was unaltered by reduction as has been previously observed with the β subunit. The clone containing the Cla I site (which lacks the first ATG codon) led to the synthesis of a protein whose mobility on gels was indistinguishable from that for the clone containing the Pst I site. On the other hand, an aberrant clone containing the newly generated ATG (above) induced the synthesis of a somewhat larger protein with an apparent $M_r$ of 33,500 (data not shown). In vitro translation of a transcript coding for the $NH_2$-terminal 21 amino acids of the β subunit led to a product precipitable by mAbβ(JRK) (FIG. 7B).

EXAMPLE 8

Expression of the Beta Subunit of $Fc_\epsilon RI$ in *E. Coli*

Figure 7C:
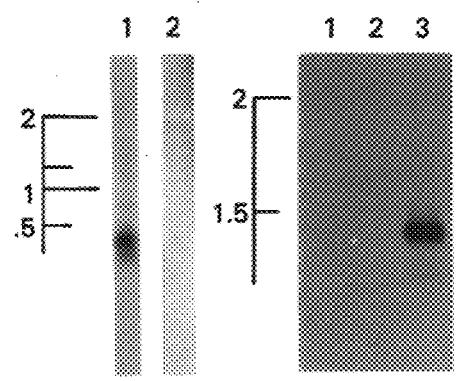
Figure 7D:
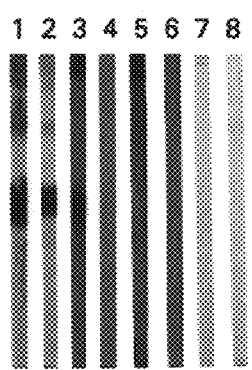

Two HinfI fragments (A, nucleotides 106–498; B, nucleotides 499–787) were individually subcloned into an *E. coli* expression vector, and extracts were prepared from the induced cultures. The results of one immunoblotting experiment are shown in FIG. 7C. The material extracted from the bacteria transformed with a vector containing the HinfI fragment B exhibited a $M_r$14,000 component reactive with mAbβ(NB) but not with mAbβ(JRK) (FIG. 7C, lane 3). The extract from the transformants containing the more $NH_2$-terminal HinfI fragment A (residues 17–148) reacted with neither antibody (compare with above). Rabbit antibodies generated by fragment A reacted on immunoblots with purified receptors exactly at the position where the two monoclonal anti-β antibodies reacted (FIG. 7D, lanes 1–3) and quantitatively precipitated intact $^{125}$I-labeled IgE-receptor complex from unfractionated detergent extracts of RBL cells (data not shown).

EXAMPLE 9

Biosynthetic Incorporation

Biosynthetic incorporation of labeled amino acids and monosaccharides was as described (Perez-Montfort et al. (1983) Biochemistry 27:5722–5728). The purification and analysis on gels and by immunoblotting of the IgE-receptor complexes have also been described (Rivera et al. (1988) Mol. Immunol., in press).

By using biosynthetic incorporation of two different amino acids labeled distinguishably, their ratio in the subunits of the receptor (Table 1, right part) was determined. The ratios of four distinctive amino acids to each other was in satisfactory agreement with the ratios predicted from the β cDNA clone (Table 1, right part, columns 1–3). Because the cDNA for the β subunit predicts three potential glycosylation sites, a double-labelling experiment using [$^3$H] mannose and [$^{35}$S]cysteine was also performed. Based on the relative carbohydrate data reported for the α subunit (Kaneilopoulos et al. (1980) J. Biol. Chem. 255:9060–9066) and correcting them on the basis of the peptide molecular weight for this chain predicted from the cDNA, it was calculated that the α subunit contains ≈20 mol of mannose per mol. It was therefore possible to determine the mannose/cysteine ratio in the β subunit from the double-labeling experiment. The results showed only 0.05 mol/mol of cysteine or 0.3 mol/mol of the β subunit (Table 1, right part, column 4).

TABLE 1

Amino Acid compositon of β Subunits cDNA versus compositional analysis for the 8 subunit

| | Asx | Thr | Ser | Glx | Pro | Gly | Ala | Val | Met | Ile | Leu | Tyr | Phe | His | Lys | Arg | Cys | Trp |
|---|---|---|---|---|---|---|---|---|---|---|---|---|---|---|---|---|---|---|
| Deduced from βcDNA | 20 | 12 | 23 | 24 | 15 | 12 | 19 | 17 | 4 | 15 | 36 | 9 | 12 | 1 | 8 | 8 | 6 | 2 |
| Direct analysis* Double-labeling studies† | 22 | 13 | 22 | 27 | 13 | 19 | 18 | 14 | 4 | 13 | 31 | 7 | 10 | 2 | 10 | 10 | 5 | ND |

| | cDNA versus incorporation data | | | |
|---|---|---|---|---|
| | Met/His | Cys/His | Cys/Trp | Man/Cys |
| Deduced from βcDNA | 4 | 6 | 3 | — |
| Direct analysis* Double-labeling studies† | 4.2 | 5.1 | 2.5 | 0.05 |

*The mol % of each amino acid as reported by Alcaraz et al. ((1987) Biochemistry 26: 2569–2575) was multiplied by 241 - the number of residues, excluding tryptophan - predicted from the cDNA. ND, not determined.
†*IgE-receptor complexes were purified from RBL cells incubated with a mixture of two precursors labeled with differentiable radioisotopes. The subunits were separated on a polyacrylamide gel. The gel was sectioned into 2-mm slices, extracted, and assayed for radioactivity by scintillation spectroscopy. The ratio of cpm of $^{35}$S/$^3$H was individually calculated for α, β, and γ subunits. The ratio in the α subunit is proportional to the known molar ratio of the $^{35}$S-labeled and $^3$H-labeled residues in the α subunit. Hence, the corresponding ratio in the β subunit (and the γ subunit) predicts the ratio of the same residues in the latter subunits.

EXAMPLE 10

Seauence Characteristics

There is ample evidence that the cDNAs that were isolated code for the β subunit. (i) In vitro transcription of the cDNA and translation of the derived mRNA produce a protein whose apparent molecular weight on gel electrophoresis is indistinguishable from that of authentic β chains (FIG. 7A). (ii) The cDNA accurately predicts the sequence of four peptides isolated from a tryptic digest of β chains (FIG. 6A) and a composition that agrees well with direct analyses and biosynthetic incorporations (Table I). (iii) Two monoclonal antibodies reactive with discrete epitopes on the α subunit (Rivera et al. (1988) Mol. Immunol., in press) precipitate the protein synthesized in vitro from the cloned cDNA (FIG. 7A), and one of them reacts with a fragment of the protein expressed in E. coli (FIG. 7C). (iv) Polyclonal antibodies raised against a fragment of the β subunit synthesized by E. coli transformants react with β chains on immunoblots (FIG. 7D) and with IgE-receptor complex in solution.

The nucleotide sequence at the 5' end of the cloned cDNA (clone 1) does not in itself define the start of the open reading frame unambiguously. There is no leader sequence and no "in frame" stop codon preceding the presumptive start codon. In addition, the molecular weight deducted from the cDNA ($M_r 27,000$) is substantially lower than the one observed on NaDodSO$_4$ gels ($M_r 32,000$), although the β subunit is not glycosylated. Therefore, it was possible that the start codon had been missed. Nevertheless, the aggregate data provide strong evidence that the full coding sequence for the β subunit has been recovered. (i) Extensive attempts failed to reveal cDNAs in either of two separate libraries with a more extended 5' sequence. (ii) The major species generated by 5' extension studies terminated precisely at the point at which most of our clones started. (iii) The second ATG codon at the 5' end meets the consensus characteristics of known initiation sites (Kozak (1987) Nucleic Acids Res. 15:8125–8148). That it is preceded by a nearby 5' ATG codon is uncommon, but not rare (Kozak (1987) Nucleic Acids Res. 15:8125–8148), and has been observed for the human α subunit (Shimizu et al. (1988) Proc. Natl. Acad. Sci. USA 85:1907–1911; Kochan et al. (1988) Nucleic Acids Res. 16:3584). (iv) As already noted, in vitro translation of an mRNA transcribed from the cDNA containing only the second ATG codon gives a polypeptide indistinguishable in length from the authentic β chains. An aberrant clone containing a start codon 48 nucleotides 5' to the presumed start codon directed the in vitro synthesis of a polypeptide with an apparent molecular weight appropriately greater than that of the β subunit. Therefore, the correspondence in apparent molecular weight between authentic β chains and the protein synthesized in vitro from clone 1 is meaningful. The RNA transfer blotting data show an mRNA of ≈2.7 kb, precisely what would be anticipated from the cDNA that was sequenced (FIG. 6), given a poly (A) tail of ≈200 nucleotides. In the discussion that follows it is assumed that the B chain begins with the methionine residue coded for by the second ATG and is, therefore, 243 residues long.

Only a single clone containing the Cla I restriction site was observed among the 37 clones analyzed. This clone likely resulted from a single base mutation during the cloning and is unlikely to represent a normally occurring mRNA. Conversely, six clones showing the deleted sequence (FIG. 6B) were observed and likely reflected an authentic species of mRNA. If translated, it would code for a $M_r 14,000$ protein with only a single transmembrane segment.

The sequence of the β subunit contains potential sites for N-linked glycosylation at residues 5, 151, and 154. However, past and new incorporation data give no evidence for carbohydrate in the β subunit (Perez-Montfort et al. (1983) Biochemistry 27:5722–5728; Holowka and Metzger (1982) Mol. Immunol. 19:219–227; and Table I). The sequence shows no unusual features or homology to previously reported sequences, in particular to those associated with Fc receptors or with Fc binding factors.

Figure 8:
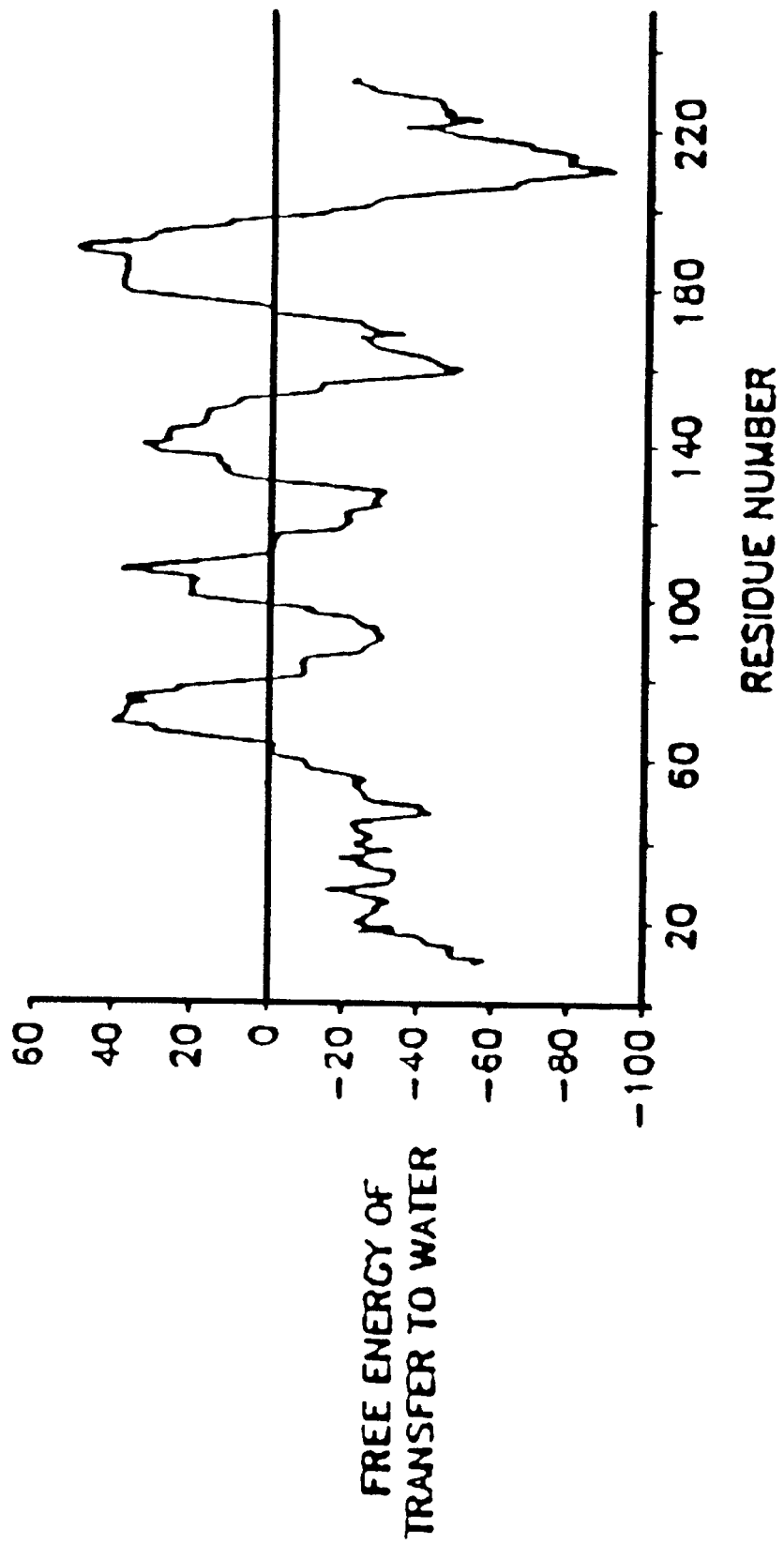
FIG. 8. Hydropathicity plot of predicted sequence for the β subunit. The procedure and hydropathicity scale recommended by Engleman et al. (Engelman et al. (1986) Annu. Rev. Biophys. Biophys. Chem. 15:321–353) was used. The net hydropathicity value for the 20 amino acids for each successive "window" is plotted at the position corresponding to the 10th residue. A net free energy of >20 kcal (1 cal=4.18 J) for transfer to water suggests a transmembrane segment (Engelman et al. (1986) Annu. Rev. Biophys. Biophys. Chem. 15:321–353).

A hydropathicity analysis suggests that the β subunit crosses the plasma membrane four times (FIG. 8). The hydrophilic NH$_2$ and COOH terminus would therefore be on the same side of the membrane. Expression of fragments of the β cDNA indicate that mAbβ-(NB) reacts within amino acids residues 149–243 (FIG. 7C) and that mAbβ(JRK) reacts with fragment containing residues 1–21 (FIG. 7B). Since neither antibody reacts appreciably with intact cells but both react strongly with cell sonicates, the combined results are consistent with the NH$_2$ and COOH terminus being on the cytoplasmic side of the plasma membrane.

Earlier studies had suggested that the β chain contained a $M_r 20,000$ "$β_1$" domain resistant to proteolysis while membrane bound (Holowka and Metzger (1982) Mol. Immunol. 19:219–227). This portion also contained those residues that were modified by an intrabilayer labeling reagent (Holowka and Metzger (1982) Mol. Immunol. 19:219–227; Holowka et al. (1981) Nature (London) 289:806–808) and became linked to the α and/or γ subunit when chemical crosslinking reagents were used (Holowka and Metzger (1982) Mol. Immunol. 19:219–227) and to the γ subunit when spontaneous disulfide linkage between the β and $γ_2$ subunits occurred (Kinet et al. (1983) Biochemistry 22:5729–5732). The remainder, "$β_2$", appeared to contain the serine residues that became phosphorylated in situ (Perez-Montfort et al (1983) Biochemistry 22:5733–5737; Quarto and Metzger (1986) Mol. Immunol. 23:1215–1223) but has never been positively identified as a discrete fragment. The sequence predicted by the cDNA for the β subunit suggests that part or all of either the NH$_2$-terminal 59 residues or the COOH-terminal 44 residues, or of both, is cleaved off to generate the β1 fragment.

EXAMPLE 11

Contransfection Experiments

The full-length coding sequences of the α and the β subunits were cotransfected in COS 7 cells by using a vector for transient expression. No IgE-binding sites were expressed at the surface of transfected cells.

Studies of the receptor with low affinity for IgE on macrophages revealed a component that could be chemically crosslinked to the IgE-binding portion and that had an apparent molecular weight similar to the β subunit of the high-affinity receptor (Finoloom and Metzger (1983) J. Immunol. 130:1489–1491). The peptides generated from this component by protease digestion appeared to differ from those released from β subunits, but it raised the possibility that other Fc receptors also contained β-like subunits that had heretofore escaped detection (Rivera et al. (1988) Mol. Immunol., in press). So far, we have no evidence for this from RNA transfer blot experiments conducted at high stringency. In particular, J774 cells are known to contain Fc$_γ$ receptors whose immunoglobulin-binding chain shows considerable homology to the α chain of the high-affinity receptor for IgE (Kinet et al. (1987) Biochemistry 26:4605–4610). However, it was not possible to detect mRNA for β chains by the methods that were employed. Similarly, NTD lymphoma cells gave negative results even though they have Fc$_γ$ receptors and show a low molecular weight component that reacts with mAbβ(JRK) on immunoblots (Rivera et al. (1988) Mol. Immunol., in press). It cannot be excluded that Fc$_γ$ receptors have β-like subunits.

EXAMPLE 12

Isolation and Sequence Analysis of Peptides of the Gamma Subunit of Fc$_ε$RI

Fc$_ε$RI was purified by affinity chromatography using TNP-lysine beads as described in G. Alcaraz et al, Biochemistry 26:2569–2575 (1987). The eluate was applied to sepharose 4B beads coupled by cyanogen bromide to monoclonal anti-β (JRK) (J. Rivera et al, Mol. Immunol. 25:647–661 (1988)). After washing the beads with 2 mM CHAPS in borate buffered saline at pH8, the bound material was eluted at 65° C. with 0.1% sodium dodecyl sulfate, phosphate buffered saline, pH 6.5. The subunits from $Fc_\epsilon RI$ were then separated by HPLC size chromatography, the β and γ containing fractions recovered, reduced, alkylated and digested with trypsin (J.-P. Kinet et al, Biochemistry 26:4605–4610 (1987)). The resulting peptides were separated by HPLC reverse phase chromatography as in J.-P. Kinet et al, Biochemistry 26:4605–4610 (1987). The chromatograms from the β and γ digests were compared and the non-overlapping γ peptides were sequenced (J.-P. Kinet et al, Biochemistry 26:4605–4610 (1987)).

EXAMPLE 13

Cloning and Sequencing of cDNA Clones of the Gamma Subunit of $Fc_\epsilon RI$ Oligonucleotide probes were synthesized according to the sequences of peptide 3 (residues 41 to 47) and of peptide 4 (residues 54 to 62). The sequences were GA(A/G)AA(A/G)TCIGA(T/C)GCTCTCTA and AA(T/C)CA(A/G)GA(A/G)ACITA(T/C)GA(A/G)ACI(T/C)TIAA. The methods used to screen the λgt11 library, to purify, subclone and sequence the positive clones are known in the art (J.-P. Kinet et al, Biochemistry 26:4605–4610 (1987)). Peptide 3 and peptide 4 were also synthesized using a peptide synthesizer ABI 431A. The purity of the synthetic peptides was assessed by HPLC reverse phase chromatography, amino acid composition and mass spectroscopy. The peptides were conjugated either to ovalbumin using m-Maleimidobenzoyl-N-hydroxysuccinimide ester (F.-T. Liu et al, Biochemistry 18:690–697 (1979)) at a molar ratio of 5:1 or to sepharose 4B with cyanogen bromide. Rabbits were immunized with the ovalbumin-conjugated peptides, the antisera collected and the antipeptide antibodies purified by affinity chromatography using sepharose 4B conjugated peptides. The antipeptide antibodies were tested for reactivity with the γ subunit of $Fc_\epsilon RI$ by Western blotting and for their ability to immunoprecipitate $^{125}I$-IgE receptor complexes (J. Rivera et al, *Mol. Immunol.* 25:647–661 (1988)).

The nucleotide sequence of the γ subunit of rat $Fc_\epsilon RI$ obtained using the method of this invention, as well as the amino acid sequence that it predicts, are shown in FIG. 9.

In order to isolate and characterize the cDNA for the γ subunit, cDNAs for the $Fc_\epsilon RI$ γ subunit were isolated from a λgt11 library prepared from rat basophilic leukemia (RBL) cells (J.-P. Kinet et al, Biochemistry 26:4605–4610 (1987)) using oligonucleotide probes. Four peptide sequences were identified in a tryptic digest of the $Fc_\epsilon RI$ γ subunits, and two of the peptides were used to synthesize two oligonucleotide probes (FIG. 9). The library was screened in duplicate with these two probes and overlapping plaques identified. Three discrete plaques were purified, subcloned and found to contain similar inserts of 0.6 to 0.7 kilobases (kb).

FIG. 9 shows the complete nucleotide sequence of the γ cDNA, the deduced amino acid sequence and the position in the sequence of the four original tryptic peptides. Analysis of the sequence (FIG. 10C) indicates an N-terminal hydrophobic signal peptide of 18 residues and a putative transmembrane domain separating a short extracellular portion of 5 residues from an intracytoplasmic domain. As predicted by earlier studies, the N-terminal processed γ subunit contains two cysteines, no methionine and no tryptophan residues (G. Alcaraz et al, Biochemistry 26:2569–2575 (1987)). Compositional analysis suggested that the γ subunit might contain one histidine residue (G. Alcaraz et al, Biochemistry 26:2569–2575 (1987)). However, recent biosynthetic dual labeling studies of the receptor using $^{35}S$ methionine and $^3H$ histidine, clearly indicated that no trace of histidine was incorporated into the receptor-associated γ subunit. Since the open reading frame derived from three independent clones, each predicts a histidine six residues from the C-terminal end, it is expected that the γ subunit undergoes a C-terminal processing which clips off the histidine-containing segment. Furthermore, because the peptide immediately preceding this histidine was recovered (FIG. 9), the C-terminal segment must be cleaved after Lys 63. The predicted molecular weight of the fully processed γ would therefore be 7139 Da, in close agreement with values obtained for the purified reduced γ on sodium dodecyl sulfate—urea gels (G. Alcaraz et al, Biochemistry 26:2569–2575 (1987)).

Polyclonal antipeptide antibodies to a heptamer and to a nonamer peptide of the γ subunit (FIG. 9) were prepared and tested for reactivity with IgE-receptor complexes for RBL cells. Both purified antipeptide antibodies reacted in a Western blot assay with the unreduced dimer and the reduced monomer of partially purified γ subunits. In addition, both antibodies quantitatively precipitated receptor-bound $^{125}I$-IgE, either from an extract of RBL cells or from a preparation of partially purified receptors. Taken together, these results leave no doubt that the cDNAs isolated according to the present invention code for the γ subunit of $Fc_\epsilon RI$.

EXAMPLE 14

Expression of Receptor

Figure 11A:
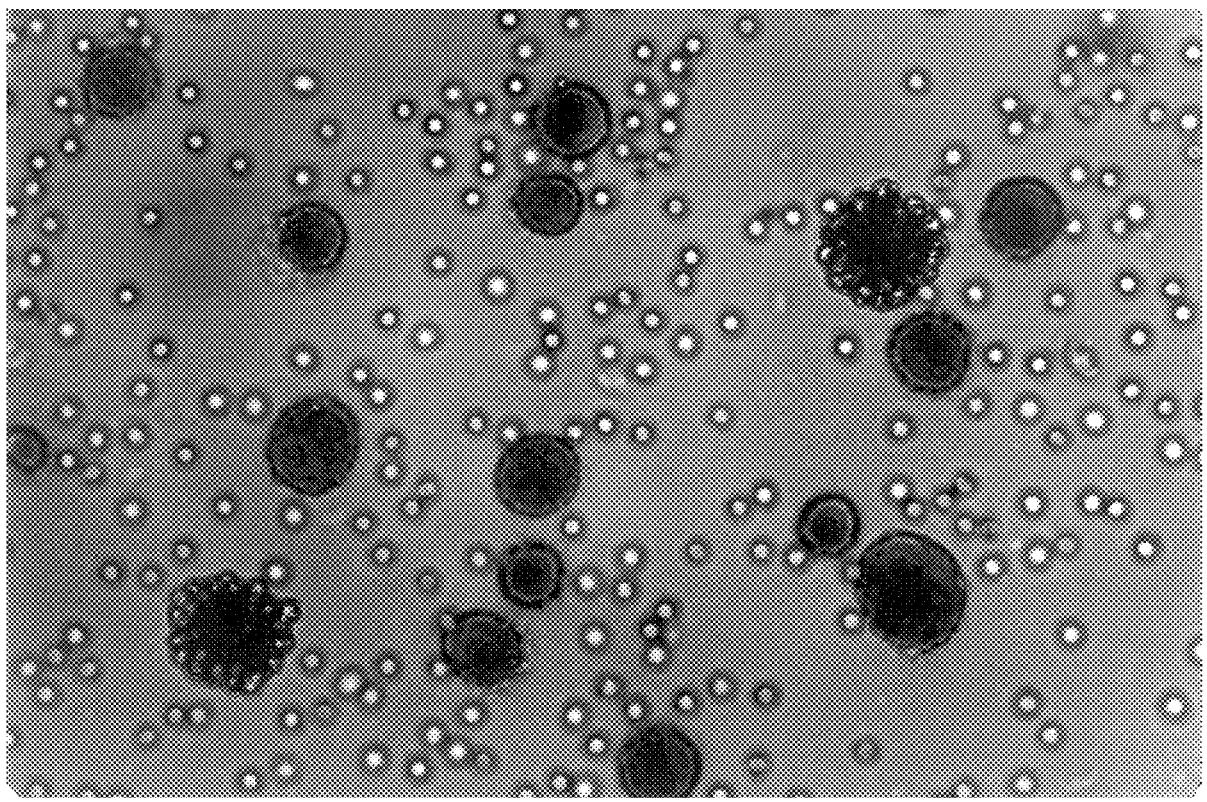
FIGS. 11A–11D. Formation of IgE rosettes by transfected COS 7 cells and RBL cells. COS 7 cells were cotransfected with the coding portions of α, β and γ cDNAs and sensitized with mouse IgE anti-DNP before being exposed to red cells derivatized with TNP (FIG. 11A). As a positive control, RBL cells were similarly tested for rosette formation (FIG. 11B). The specificity of the rosetting assay was assessed by preincubating the cotransfected COS 7 cells (FIG. 11B) and RBL cells (FIG. 11D) with rat IgE (which lacks the anti-DNP activity) prior to the addition of the mouse anti-DNP IgE.
Figure 11B:
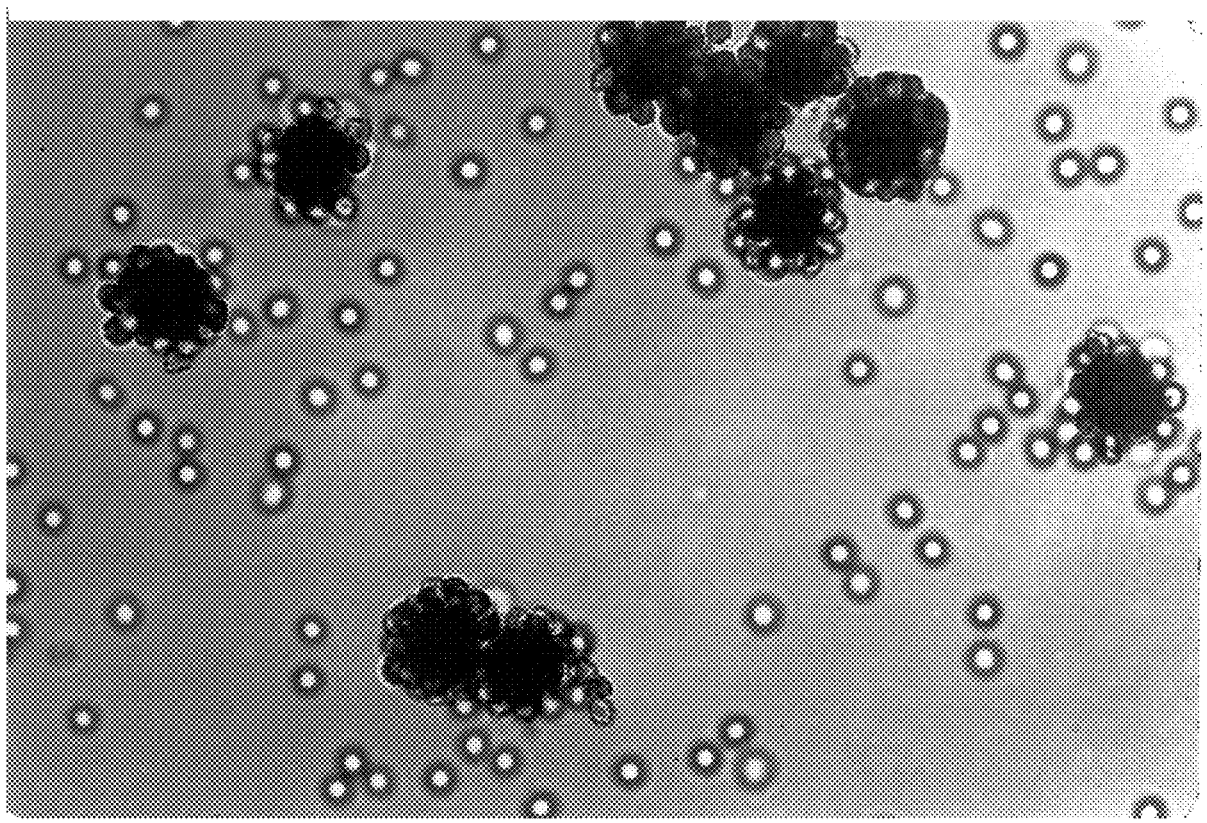
Figure 11C:
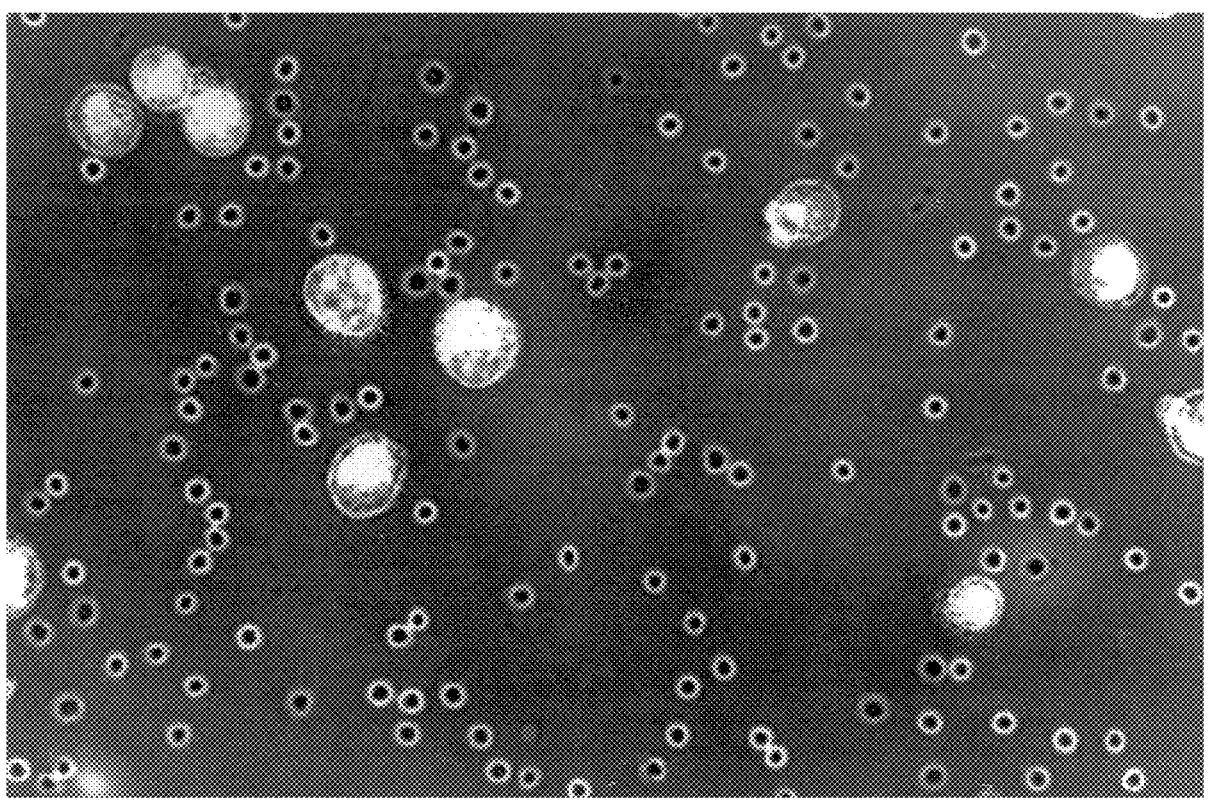
Figure 11D:
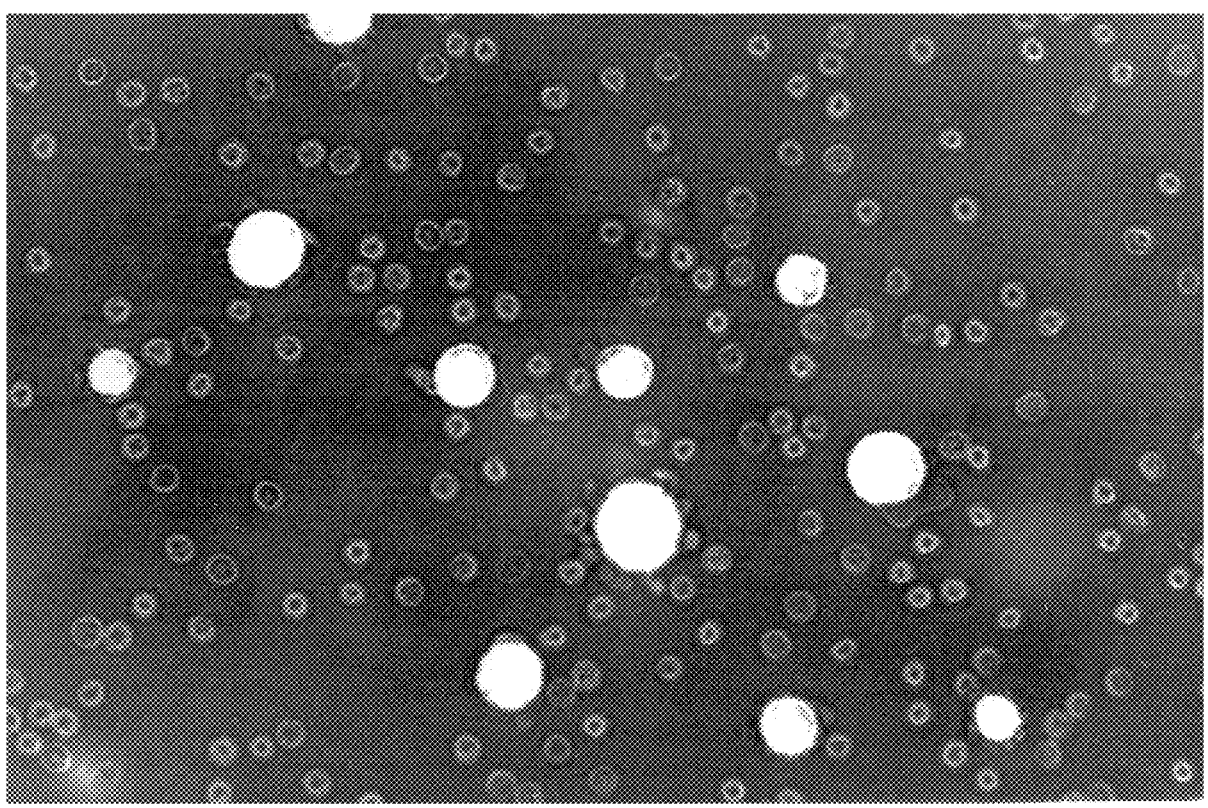
Figure 12A:
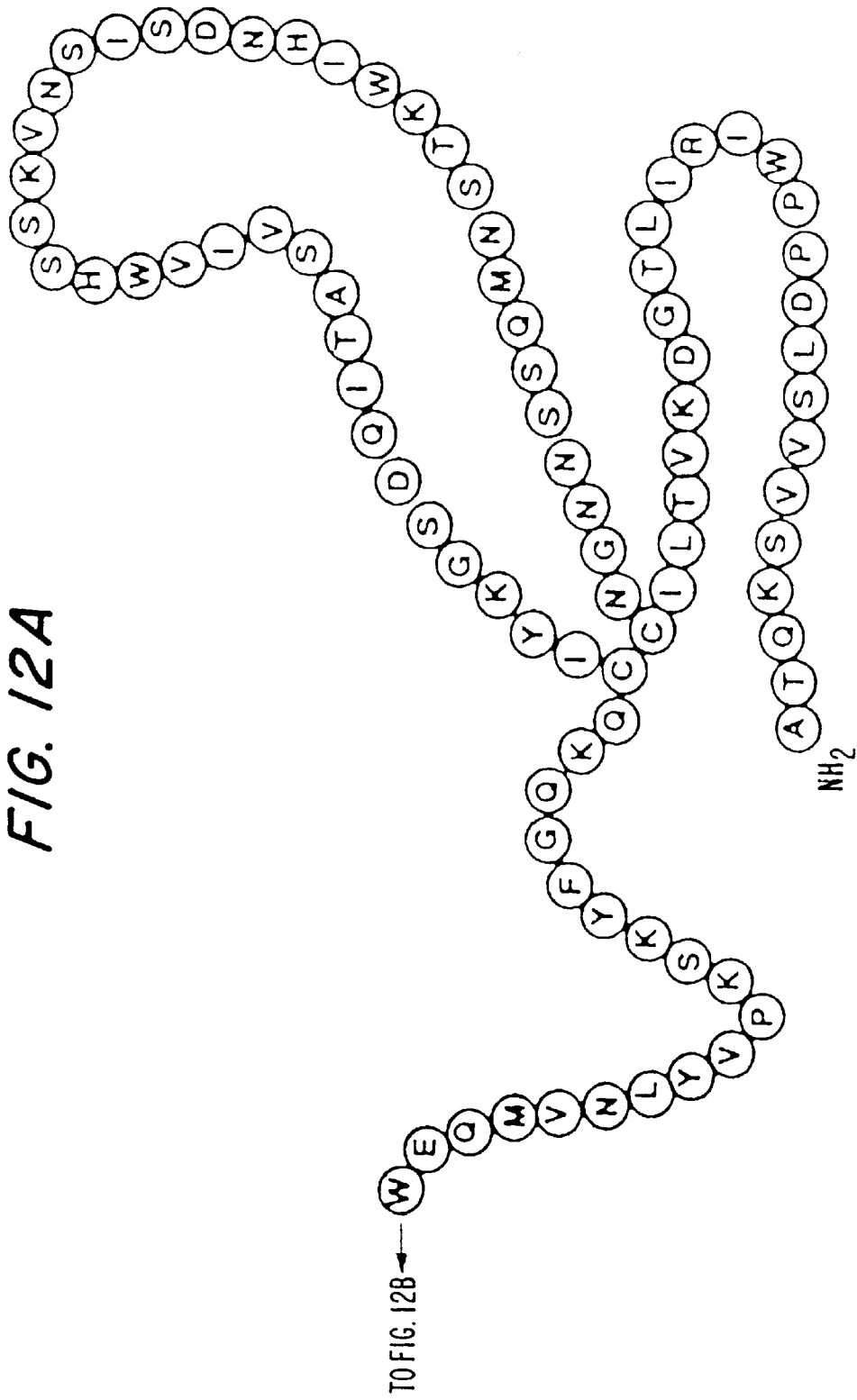
FIG. 12. Model of the tetrameric high affinity receptor for IgE. The polypeptides are shown in their fully processed form. The receptor is oriented such that the large extracellular portion of the α subunit is shown at the top and the remainder of the chain on the left. To the right of the α subunit is the β subunit with its four transmembrane segments and to the right of it, the dimer of γ chains. Cysteines 26 and 68 and cysteines 107 and 151 in the α chain are paired as they are likely to be disulfide linked, as are the homologous cysteines in the Fc$_\gamma$ receptors (M. Hibbs et al, J. Immunol. 140:544–550 (1988)). The putative transmembrane segments have all been shown as consisting of 21 residues and would be expected to be in an α-helical conformation. The single letter code for amino acids is used (M. Dayhoff et al, in Atlas of Protein Sequence and Structure, Suppl. 3, ed. M. Dayhoff, 363–373, Natl. Biomed. Res. Fndtn., Washington D.C. (1978)). Every 10th residue (starting from the N-terminus) is shaded.
Figure 12B:
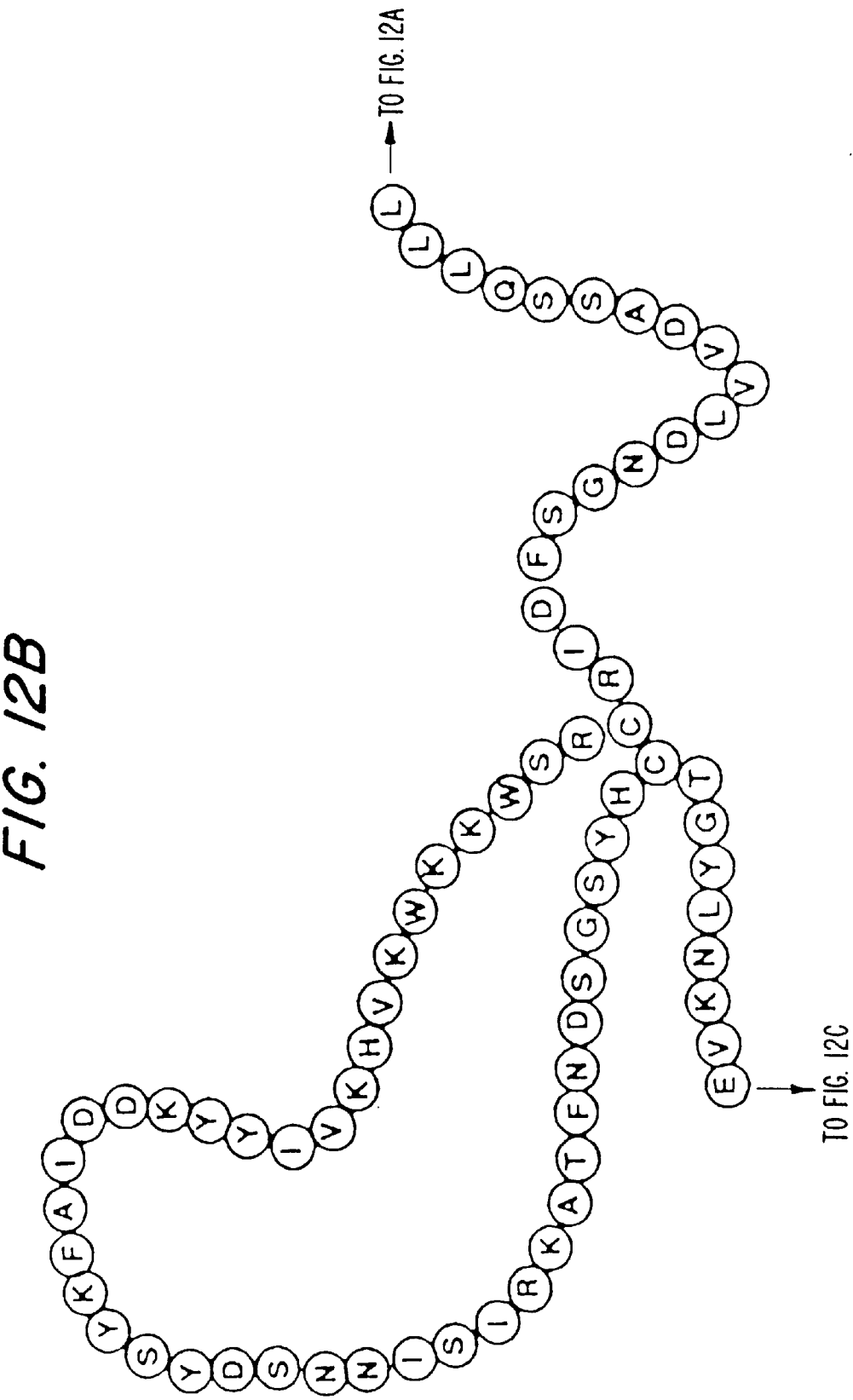
Figure 12C:
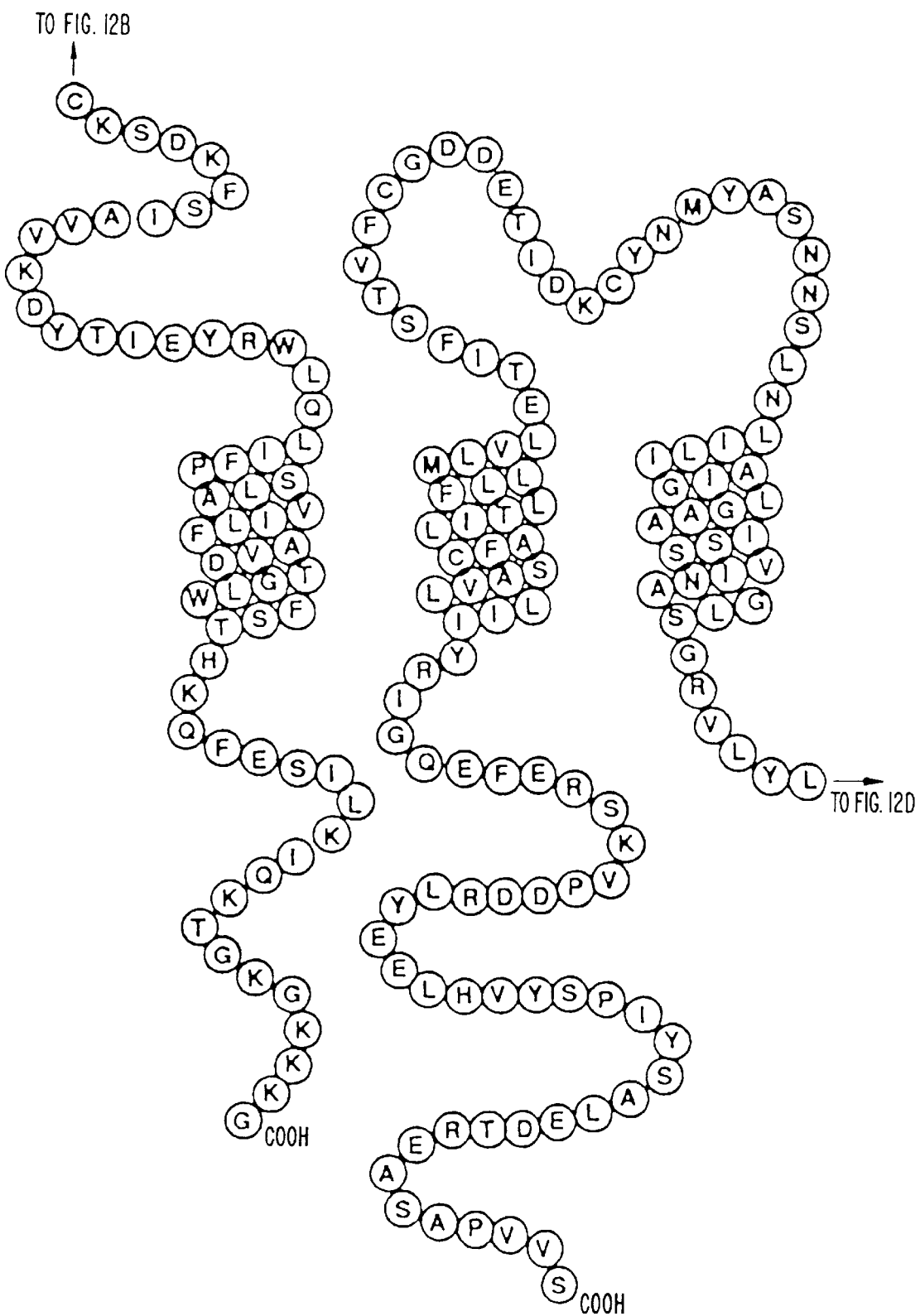
Figure 12D:
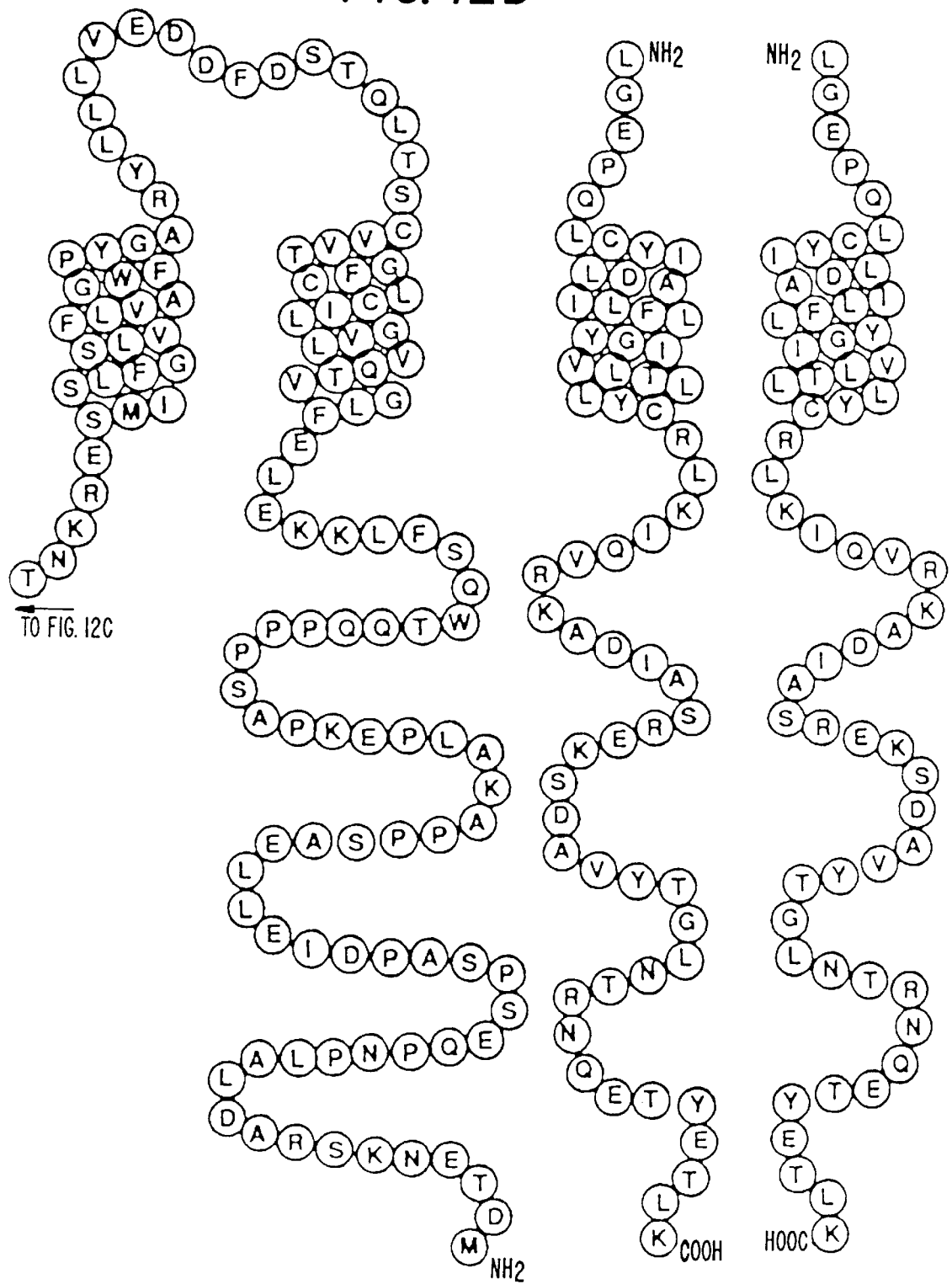

In order to achieve expression of the receptor on the surface of COS 7 cells, the coding region of the α, β, and γ cDNAs were first subcloned separately into the SV 40 promoter-driven expression vector pSVL, prior to transfection into the COS-7 cells. The 810 bp EcoRI-Sty I restriction fragment of the α cDNA, the 965 bp EcoRI-EcoRV restriction fragment of the β cDNA and the 300 bp EcoRI-Dde I restriction fragment of the γ cDNA were subcloned separately into the Sma I site of the transient expression vector pSVL (Pharmacia, Uppsala, Sweden). These restriction fragments individually contained the entire coding sequence of the appropriate subunit and variable portions of untranslated sequences. The only foreign sequence was the starting EcoRI recognition sequence which belonged to the initial linker. Cultured COS 7 monkey kidney cells were then transfected with 40 μg of DNA by the standard calcium phosphate precipitation technique (L. Davis et al, in Basic Methods in Molecular Biology, ed. L. Davis, Elsevier, N.Y. (1986)). After 48 hrs, the transfected cells (panels A and B of FIG. 11), as well as RBL cells (panels C and D of FIG. 11), were examined for surface expression of IgE binding by an IgE resetting assay. The cells ($5 \times 10^6$ cells/ml) were incubated at room temperature with (panels B and D) or without (panels A and C) 50 μg/ml of non-specific rat IgE for 30 min and then with 5 μg/ml of anti-DNP-IgE (F.-T. Liu et al, J. Immunol. 124:2728–2736 (1980)). The cells were then rosetted with ox red blood cells that had been modified with 2,4,6-trinitrobenzene sulfonic acid according to a known method (M. Rittenberg et al, Proc. Soc. Exp. Biol. Med. 132:575–581 (1969)). The results are shown in FIG. 11. FIG. 11A shows IgE-binding activity expressed by cells cotransfected with the α, β and γ subunits. Virtually all RBL cells, used as a positive control, formed rosettes (FIG. 11C). The rosettes were completely inhibited by preincubation of the cells with rat IgE (FIGS. 11B and D) but not with human IgE (not shown). This coincides with the species specificity for the rat $Fc_\epsilon RI$ (A. Kulczycki et al, J. Exp. Med. 139:600–616 (1974)).

In order to study the requirements for surface expression of IgE-binding activity, the cells were transfected with different combinations of the cDNAs for the three subunits, as shown in Table 2.

COS-7 cells were transfected with different combinations of cDNAs for the three subunits of Fc$_\epsilon$RI (FIG. 11). The rosetting assay was performed for each transfection shown in Table 2. The assessment of the mRNA by Northern blotting was performed one time only (on 2×10$^7$ cells). Inhibitor was added to the cells in the experiments marked by an asterisk in Table 2 (50 μg/ml of non-specific rat IgE was added to the cells 30 minutes prior to the addition of the specific mouse anti-DNP IgE).

TABLE 2

Transfection Experiments

| | | | | Expression |
|---|---|---|---|---|
| Cells | Transfections cDNA | No. | Receptor mRNA | IgE Binding (rosettes/cells counted) |
| COS 7 | 0 | 9 | 0 | 0/12,948 |
| | α | 2 | α | 0/4,050 |
| | αβ | 2 | αβ | 0/3,504 |
| | αγ | 4 | α | 0/8,030 |
| | β | 1 | β | 0/2,069 |
| | αβγ | 29 | αβγ | 920/41,238 |
| | αβγ | 4 | αβγ | 0/7,542* |
| RBL | 0 | — | αβγ | "100%" |

*Experiments where inhibiter was added.

Table 2 summarizes the data derived from all the transfection experiments performed by the present inventors to the time of filing the present application. The success rate of the transfection experiments has improved so that there is now routinely achieved 5±2% expression of IgE binding when α, β and γ are simultaneously cotransfected.

Successful transfection was achieved for all combinations, as assessed by Northern blotting, but rosette forming cells were only detected after cotransfection of the full set of the cDNAs. These results indicate that the β and γ subunits are required for surface-expression of the IgE-binding α subunit. It is further indicated that only the fully assembled receptor reaches the plasma membrane. This phenomenon has also been observed in other systems (M. McPhaul et al, Proc. Natl. Acad. Sci. USA 83:8863–8867 (1986); Y. Minami et al, Proc. Natl. Acad. Sci. USA 84:2688–2692 (1987)) and may be generally applicable to polymeric membrane proteins.

The easy dissociability of β and γ$_2$ from α (B. Rivnay et al, Biochemistry 21:6922–6927 (1982)) has raised persistent uncertainty about whether conceptually, γ$_2$ and β should be considered as subunits of Fc$_\epsilon$RI or as "receptor associated" proteins. (An example of the latter is the CD3 complex which associates with the antigen receptor on thymus-derived lymphocytes (H. Clevers et al, Ann. Rev. Immunol. 6:629–662 (1988)). The subunit model for Fc$_\epsilon$RI has been favored, for example, on the basis of the coordinate biosynthesis and catabolism of α, β and γ$_2$ (R. Quarto et al, Molec. Immunol. 22:1045–1052 (1985)). The new data on transfected cells obtained by the present invention provides the strongest evidence yet obtained that αβγ$_2$ is the minimal structure for Fc$_\epsilon$RI.

The present model for the tetrameric Fc$_\epsilon$RI receptor is illustrated in FIG. 12. In this model each of the 589 amino acid residues of which the expressed receptor is composed is shown as a circle. In the diagram, the exterior of the cell would be at the top, the plasma membrane in which the receptor is embedded would be in the middle, and the interior of the cell towards the bottom. Each of the polypeptide chains (the α on the left, the β chain in the middle and the two γ chains on the right) contains one or more transmembrane segments.

The α chain is believed to contain two intrachain disulfide loops, and the sequences of these loops show considerable homology with immunoglobulins (J.-P. Kinet et al, Biochemistry 26:4605 (1987); A. Shimizu et al, Proc. Natl. Acad. Sci. USA 85:1907 (1988); J. Kochan et al, Nucleic Acids Res. 16:3584 (1988)). Thus, the α subunit is another member of the immunoglobulin superfamily (A. Williams et al, Ann. Rev. Immunol. 6:381 (1988)). The extracellular and transmembrane segments of the α chain show considerable homology with the immunoglobulin binding chain of Fc receptors that bind IgG (J. Ravetch et al, Science 234:178 (1986)) but the intracellular cytoplasmic tail is quite different. The carbohydrate residues that are covalently attached to the extracellular portion of the α chain are not indicated in FIG. 12. There are seven potential sites for N-linked carbohydrates (J.-P. Kinet et al, Biochemistry 26:4605 (1987); A. Shimizu et al, Proc. Natl. Acad. Sci. USA 85:1907 (1988)), but which of these that are actually used by the cell remains to be determined. Studies show that the carbohydrate is not essential for the binding of IgE by this chain (B. Hempstead et al, J. Biol. Chem. 256:10717 (1981)).

The β chain contains four transmembrane segments (J.-P. Kinet et al, Proc. Natl. Acad. Sci. USA 85:6483 (1988)) and previous studies with monoclonal antibodies (J.-P. Kinet et al, Proc. Natl. Acad. Sci. USA 85:6483 (1988); J. Rivera et al, Mol. Immunol. 25:647 (1988)) show that the amino- and carboxyl-termini which are respectively 59 and 43 residues long, protrude from the cytoplasmic face of the plasma membrane. Similarly, the γ chains have an extensive intracellular extension but only very limited exposure to the exterior.

According to the present model, the putative transmembrane domains of the individual subunits are predicted from their respective hydropathicity plots (see FIG. 10, wherein a net free energy of >20 kcal/mol for transfer to water suggests a transmembrane segment or a leader peptide (D. Engelman et al, Ann. Rev. Biophys. Biophys. Chem. 15:321–353 (1986)). These plots suggest one, four and one hydrophobic domains for the α, β and each γ, respectively (i.e., seven transmembrane domains for the entire receptor). Members of a family of receptors interacting with G proteins also contain seven transmembrane domains (I. Herskowitz et al, Cell 50:995–996 (1987)). This family includes β and α adrenergic, muscarinic receptors and rhodopsin. Although no sequence homology between Fc$_\epsilon$RI and these receptors is found, it is significant that an interaction between Fc$_\epsilon$RI and G proteins has been postulated to explain at least some of the biochemical pathways activated by this receptor (S. Cockcroft et al, Nature 314:534–536 (1985)). The topology of the α and β subunits has been discussed in J.-P. Kinet et al, Biochemistry 26:4605–4610 (1987) and A. Shimizu et al, Proc. Natl. Acad. Sci. USA 85:1907–1911 (1988), in particular, the cytoplasmic localization of the C- and N-terminal portions of the β subunit. Two pieces of evidence support the topology of the γ-dimer as shown in FIG. 12: The γ can be oxidatively iodinated on inverted vesicles but not on intact cells (D. Holowka et al, J. Biol. Chem. 259:3720–3728 (1984)) and, in vivo, γ becomes phosphorylated on threonine residues (R. Quarto et al, Mol. Immunol. 23:1215–1223 (1986)). None of the relevant residues are present in the small presumptive extracytoplasmic segment of γ but all are present on the presumptive cytoplasmic tail, i.e., two tyrosine and four threonine residues.

As a further means to examine the topology of the receptor, the putative extracellular and intracellular segments of the three subunits were analyzed for their relative content of basic residues, as suggested by G. von Heijne Biochim. Biophys. Acta 947:307–333 (1988). He found the ratio of basic/total residues varies as a function of the length of the segment studied, but in general was substantially higher in the non-translocated (intracellular) segments than in the translocated (extracellular) segments of membrane proteins. Table 3 below shows a good correspondence between the ratios calculated for the present model and the ratios expected on the basis of "known" membrane proteins (G. von Heijne, Biochim. Biophys. Acta 947:307–333 (1988)), thereby providing independent support for the topological model presented here.

β and γ subunits of $Fc_\epsilon RI$ (J.-P. Kinet et al, Biochemistry 24:4117–4124 (1985)). It seems reasonable to speculate that such hypothetical components would be homologous to β or γ, or both. The availability of genetic probes for the latter components will now permit an in-depth exploration of this possibility.

The success in expression of IgE binding achieved according to the present invention has important therapeutic implications. Degranulation of mast cells and basophils triggered by $Fc_\epsilon RI$ accounts for many of the symptoms of allergy. Given the high incidence of this disorder, the dis-

TABLE 3

Ratio Lys + Arg/total in Translocated and Untranslocated Segments of Receptor Subunits

| Polypeptide | | Extracellular (translocated) | | | | Intracellular (untranslocated) | | |
|---|---|---|---|---|---|---|---|---|
| | | No. residues | Ratio found | Ratio expected | | No. residues | Ratio found | Ratio expected |
| α | | 179 | 0.13 | 0.11 | | 22 | 0.31 | 0.19 |
| β | Loop 1 | 17 | 0.06 | 0.04 | N-term | 59 | 0.10 | 0.10 |
| | Loop 3 | 28 | 0.03 | 0.04 | Loop 2 | 12 | 0.25 | 0.20 |
| | | | | | C-term | 43 | 0.12 | 0.18 |
| γ | | 5 | 0 | 0.08 | | 36 | 0.22 | 0.16 |
| $\alpha\beta\gamma_2$ | | 234 | 0.045 | 0.02–0.06 | | 208 | 0.17 | 0.12–0.16 |

The expected values calculated from the data in FIG. 8 of G. von Heijne, Biochim. Biophys. Acta 947, 307–333 (1988), in which the ratio found for the extra-membrane segments from "known" proteins has been plotted as a function of the segments' length.

The present model clarifies several important features with respect to the organization of the subunits. The β and dimer of γ interact with each other; in detergent solutions they dissociate from the α as a unit before dissociating from each other (J. Rivera et al, Mol. Immunol. 25:647–661 (1988)), and occasionally, β and the γ dimer are observed to be disulfide-linked to each other (J.-P. Kinet, Biochemistry 22:5729–5732 (1983)). The likeliest candidates for this bond are γ-cys7 and β-cys80 which are predicted to be topologically close. This would then require that at least the γ-cys26 residues are disulfide-linked in the γ dimer. Preliminary data on the receptor biosynthesis suggest that α and β interact with each other.

The functional properties of $Fc_\epsilon RI$ are broadly similar to those of several $Fc_\gamma R$. $Fc_\gamma R$ appears to bind to homologous segments of the immunoglobulin's Fc region (B. Helm et al, Nature 331:180–183 (1988); A. Duncan et al, Nature 332:563–564 (1988)), and the binding site on the receptor is found on a homologous polypeptide having immunoglobulin-like domains (J.-P. Kinet et al, Biochemistry 26:4605–4610 (1987); J. Ravetch et al, Science 234:718–725 (1986)). Both types of receptors need to be aggregated to initiate cell activation and, where studied, the latter appears to involve generation of broadly similar second messengers (H. Metzger et al, Ann. Rev. Immunol. 4:419–470 (1986); N. Hogg, Immunol. Today 9:185–187 (1988)). It is surprising, therefore, that whereas $Fc_\epsilon RI$ consists of four polypeptide chains, seven transmembrane segments and five cytoplasmic segments, $Fc_\gamma Rs$ appear to perform similar functions with a much simpler structure, i.e., an α-like subunit alone. The extreme case is that of $Fc_\gamma RIII$ which appears to lack even transmembrane and intracellular segments (P. Selvaray et al, Nature 333:565–567 (1988); D. Simmons et al, Nature 333:568–570 (1988); T. Huizinga et al, Nature 333:667–669 (1988)). It has been suggested that additional components of $Fc_\gamma$ receptors may have thus far been missed. Possibly such components are even more easily lost upon solubilization of the receptors than are the covery of a specific inhibitor of IgE binding is expected to yield enormous therapeutic benefits. The development of such an inhibitor has been hampered by the lack of a practical in vitro assay for the binding of human IgE to the human receptors. For example, a recent assessment of IgE-derived peptides of their inhibitory capacity had to be determined by skin-testing (B. Helm et al, Nature 331:180–183 (1988)), a cumbersome and potentially dangerous procedure.

That the present invention achieves the expression of the transfected rodent receptor indicates that human $Fc_\epsilon RI$ can be similarly expressed. Alternatively, since at present only the cDNA coding for the human α subunit has been isolated (A. Shimizu et al, Proc. Natl. Acad. Sci. USA 85:1907–1911 (1988); J. Kochan et al, Nucl. Acids Res. 16:3584 (1988)), it is expected that it can be expressed in cotransfections with the cDNAs coding for the rodent β and γ chains.

A comparison between the human and rat α subunits is set forth in Table 4 below.

TABLE 4

Comparative Properties of Human and Rat Alpha Chains

| | Species | | |
|---|---|---|---|
| Domain | Human | Rat | % Homology |
| Extracellular | 180 | 181 | 49 |
| Transmembrane | 21 | 21 | 67+ |
| Intracellular | 31 | 20 | 23 |
| Total | 232 | 222 | 47* |

* Wt ave.
+ Human: WLQFFIPLLVVILFAVDTGLFISTQQQ
Rat: WLQLIFPSLA<u>VILFAVDTGL</u>WFSTHKQ It may be seen from the above Table that there is an overall homology between the human and rat alpha chains of about 47%, but an almost 70% homology in the presumed transmembrane domains. Indeed, when the transmembrane domains are examined closely, there is a stretch of 10 consecutive residues that are completely identical. This stretch of consecutive residues is underlined in Table 4.

Since the transmembrane segment is the region of the α chain that is most likely to interact with the β and γ chains, it was expected that the human α chain would be expressible, if transfected, along with the rat β and γ chains. This has proved to be the case as the present inventors have been able to express human IgE binding by COS cells transfected simultaneously with the human a and the rat β and γ subunits. It will be advantageous, of course, to have permanently transfected cell lines and for such lines, one will want to utilize the human β and γ subunits. The present inventors are in the process of identifying the coding sequences for these subunits so that preparing such transfectants will be straightforward. Thus, with the materials available now, it is already practical to search for peptide inhibitors of human IgE binding in vitro. To make the assay suitable for truly mass screening of drugs will require only minor extensions of the present work.

The genetic work, of course, provides much more than an assay, as important as the latter may be. Through directed mutation it will, in addition, allow the development of further information regarding the critical binding regions. It is expected that, using this information, rational drug design will become possible. It is further expected that it will be possible to block the function of the receptor itself, i.e., it will be possible to interfere with the early biochemical signals that result from activation of the receptor.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed:

1. An isolated nucleic acid molecule encoding a beta subunit of rat Fc$_\epsilon$RI, said beta subunit having an amino acid sequence of at least amino acid residues 1–107, as shown in FIG. 6A.

2. The nucleic acid molecule of claim 1 wherein said molecule comprises at least nucleotides 55–375 of a nucleotide sequence as shown in FIG. 6A.

3. The nucleic acid molecule of claim 1, wherein said amino acid sequence comprises at least amino acid residues 1–243, as shown in FIG. 6A.

4. The nucleic acid molecule of claim 3, wherein said nucleic acid molecule comprises at least nucleotides 55–783 of a nucleotide sequence as shown in FIG. 6A.

5. A recombinant vector including a nucleic acid molecule according to claim 4.

6. A transgenic cell produced by introducing into a cell a vector according to claim 5.

7. A recombinant vector including a nucleic acid molecule according to claim 3.

8. A transgenic cell produced by introducing into a cell a vector according to claim 7.

9. A method of expressing a functional rat Fc$_\epsilon$RI in a host cell, comprising introducing into a host cell capable of expressing α and γ subunits of rat Fc$_\epsilon$RI a nucleic acid molecule according to claim 3, and culturing the cell under conditions whereby a functional rat Fc$_\epsilon$RI is expressed.

10. A method of expressing a functional rat Fc$_\epsilon$RI in a host cell, comprising introducing into the host cell nucleic acid molecules encoding
  (a) an α subunit of rat Fc$_\epsilon$RI;
  (b) a β subunit of rat Fc$_\epsilon$RI; and
  (c) a γ subunit of rat Fc$_\epsilon$RI wherein said β subunit is encoded by a nucleic acid molecule according to claim 3.

11. The nucleic acid molecule of claim 1, wherein said amino acid sequence comprises amino acid residues 1–107 of FIG. 6A followed by amino acid residues 1–5 of an amino acid sequence shown in FIG. 6B.

12. A recombinant vector including a nucleic acid molecule according to claim 11.

13. A transgenic cell produced by introducing into a cell a vector according to claim 12.

14. A recombinant vector including a nucleic acid molecule according to claim 1.

15. A transgenic cell produced by introducing into a cell a vector according to claim 14.

16. A cell according to claim1 15 wherein the cell is a bacterial cell.

17. A cell according to claim 15 wherein the cell is a eukaryotic cell.

18. A cell according to claim 17 wherein the cell is a mammalian cell.

19. A method of producing a beta subunit of rat Fc$_\epsilon$RI, the method comprising growing a cell according to claim 15 under conditions whereby the nucleic acid molecule is expressed, resulting in the synthesis of said beta subunit in the cell.

20. The method of claim 19 further comprising purifying the beta subunit from the cell.

21. An isolated nucleic acid molecule including at least 15 contiguous nucleotides of the nucleotides 55–375 shown in FIG. 6A, or at least 15 contiguous nucleotides of a complement of nucleotides 55–375.

22. A recombinant vector including a nucleic acid molecule according to claim 21.

23. A transgenic cell produced by introducing into a cell a vector according to claim 22.

24. A recombinant vector including a nucleic acid molecule according to claim 21.

25. A transgenic cell produced by introducing into a cell a vector according to claim 24.

26. An isolated nucleic acid molecule including at least 18 contiguous nucleotides of a DNA sequence shown in FIG. 6A, or the complement of said sequence.

27. The isolated nucleic acid molecule of claim 26, including at least 20 contiguous nucleotides of the DNA sequence shown in FIG. 6A, or the complement of said sequence.

28. The isolated nucleic acid molecule of claim 26, including at least 26 contiguous nucleotides of the DNA sequence shown in FIG. 6A, or the complement of said sequence.

* * * * *

UNITED STATES PATENT AND TRADEMARK OFFICE
CERTIFICATE OF CORRECTION

PATENT NO. : 6,165,744
DATED : December 26, 2000
INVENTOR(S) : Kinet et al.

It is certified that error appears in the above-identified patent and that said Letters Patent is hereby corrected as shown below:

Column 1,
Line 5, insert -- BACKGROUND OF THE INVENTION --
Line 14, delete "BACKGROUND OF THE INVENTION"

Column 2,
Line 56, reads "FIG. 1." should read -- FIGS. 1A-1C --

Column 3,
Line 21, reads "(A)(2)-(6)" should read -- (A-F) --
Lines 23 and 28, reads "6B" should read -- 6G --
Line 30, reads "A" should read -- B --

Column 4,
Line 39, reads "(panel A)" should read -- (FIG. 10A) --
Line 39, reads "(panel B)" should read -- (FIG. 10B) --
Line 40, reads "(panel C)" should read -- (FIG. 10C) --
Line 50, reads "(FIG. 11B)" should read -- (FIG. 11C) --
Line 56, reads "FIG. 12." should read -- FIGS 12A-12D --

Column 5,
Lines 17-18, reads "FIGS. 1, 6 or 9," should read -- FIGS. 1A-1C, 6A-6G, or 9, --
Line 23, reads "1,6 or 9," should read -- 1A-1C, 6A-6G, or 9, --
Line 30, reads "FIGS. 1, 6, or 9," should read -- FIGS. 1A-1C, 6A-6G, or 9, --

Column 6,
Line 35, reads "PGEM" should read -- pGEM --
Line 48, reads "FIG. 1." should read -- FIGS. 1A-1C --

Column 7,
Line 64, reads "Prokarvotic" should read -- Prokaryotic --

UNITED STATES PATENT AND TRADEMARK OFFICE
CERTIFICATE OF CORRECTION

PATENT NO. : 6,165,744
DATED : December 26, 2000
INVENTOR(S) : Kinet et al.

It is certified that error appears in the above-identified patent and that said Letters Patent is hereby corrected as shown below:

Column 9,
Line 23, reads "(FIG. 6A)." should read -- (FIGS. 6A-6F). --
Line 37, reads "(FIG. 6B)." should read -- (FIG. 6G). --
Line 41, reads "(FIG. 6A)." should read -- (FIG. 6B). --
Line 43, reads "6A" should read -- 6A-6F --

Column 11,
Line 40, Table 1, reads "$^{\dagger}$*IgE" should read -- ↑IgE --

Column 12,
Line 27, Table 1, reads "8" should read -- β --
Line 55, reads "Seavence" should read -- Sequence --
Line 63, reads "(FIG. 6A)" should read -- (FIGS. 6A-6F) --
Line 66, reads "α" should read -- β --
Line 50, reads "(FIG. 6B)" should read -- (FIG. 6G --

Column 13,
Line 41, reads "(FIG. 6A)" should read -- (FIGS. 6A-6F) --
Line 43, reads "B" should read -- β --
Line 50, reads "(FIG. 6B)" should read -- (FIG. 6G) --

Column 16,
Lines 47-48, reads "(panels A and B of FIG. 11)" should read -- (FIGS. 11A and 11B) --
Lines 48-49, reads "(panesl C and D of FIG. 11)" should read -- (FIGS. 11C and 11D) --
Line 50, reads "resetting" should read -- rosetting --
Line 51, reads "(panels B and D)" should read -- (FIGS. 11B and 11D) --
Line 52, reads "(panels A and C)" should read -- (FIGS. 11A and 11C) --

Column 17,
Line 62, reads "FIG. 12" should read -- FIGS. 12A-12D --

Column 18,
Lines 17 and 55, reads "FIG. 12" should read -- FIGS. 12A-12D --
Line 36, reads "FIG. 10," should read -- FIGS. 10A-10C), --

Column 21,
Line 12, reads "a" should read -- α --
Lines 41 and 44, reads "FIG. 6A" should read -- FIGS. 6A-6B --
Lines 47 and 50, reads "FIG. 6A" should read -- FIGS. 6A-6C --

UNITED STATES PATENT AND TRADEMARK OFFICE
CERTIFICATE OF CORRECTION

PATENT NO. : 6,165,744
DATED : December 26, 2000
INVENTOR(S) : Kinet et al.

It is certified that error appears in the above-identified patent and that said Letters Patent is hereby corrected as shown below:

Column 22,
Lines 14 and 38, reads "FIG. 6A" should read -- FIGS. 6A-6B --
Line 15, reads "FIG. 6B" should read -- FIG. 6G --
Line 24, reads "claim 1" should read -- claim --
Lines 50, 53 and 56, reads "FIG. 6A" should read -- FIGS. 6A-6F --

Signed and Sealed this

Sixth Day of May, 2003

JAMES E. ROGAN
*Director of the United States Patent and Trademark Office*